United States Patent [19]

Fischer et al.

[11] Patent Number: 5,393,729
[45] Date of Patent: Feb. 28, 1995

[54] 3-ARYL-PYRONE DERIVATIVES

[75] Inventors: Reiner Fischer, Monheim; Andreas Krebs, Odenthal; Folker Lieb, Leverkusen; Michael Ruther, Monheim; Jörg Stetter, Wuppertal; Christoph Erdelen, Leichlingen; Ulrike Wachendorff-Neumann, Monheim; Klaus Lürssen, Bergisch Gladbach; Hans-Joachim Santel, Leverkusen; Robert R. Schmidt, Bergisch Gladbach, all of Germany

[73] Assignee: Bayer Aktiengesellschaft, Leverkusen, Germany

[21] Appl. No.: 116,790

[22] Filed: Sep. 3, 1993

[30] Foreign Application Priority Data

Sep. 10, 1992 [DE] Germany ........................ 4230267
Mar. 17, 1993 [DE] Germany ........................ 4308451

[51] Int. Cl.⁶ ............... C07D 309/38; C07D 311/74; C07D 493/04; A01N 43/16
[52] U.S. Cl. ..................... 504/128; 504/140; 514/451; 514/456; 514/457; 544/149; 546/207; 546/268; 549/23; 549/50; 549/60; 549/216; 549/285; 549/291; 549/292
[58] Field of Search ............ 549/291, 292, 216, 285, 549/23, 50, 60; 504/140, 128; 514/456, 457

[56] References Cited

U.S. PATENT DOCUMENTS 2,884,427  4/1959  Emerson et al. ............... 549/285 X

FOREIGN PATENT DOCUMENTS 0483582  5/1992  European Pat. Off. .
1593373  7/1970  Germany .

OTHER PUBLICATIONS

Chemical Abstracts, vol. 57, No. 10, 12 Nov. 1962, Abstract No. 12418b.
Registry Handbook CAS 1985, RN: 98054-07-0.
Bulletin de la Societe Chimique de France 1962, Paris, FR, pp. 365-369.
Chemical Abstracts, vol. 109, No. 19, 7 Nov. 1988, Abstracts No. 170174w.
Chemical Abstracts, vol. 86, No. 23, 6 Jun. 1977, Abstract No. 167911k.
Barton et al, *J. Chem. Soc. Perkin Trans. 1*, 1992, pp. 1365–1375.
Van Zanten et al, *Chemical Abstracts*, 61:4303e-g (1964).
Wagh et al, *Ind. J. Chem.*, vol. 14B, Nov. 1976, pp. 861–863.

*Primary Examiner*—Robert W. Ramsuer
*Assistant Examiner*—Fiona T. Powers
*Attorney, Agent, or Firm*—William C. Gerstenzang

[57] ABSTRACT

The invention relates to 3-aryl-pyrone derivatives of the general formula (I)

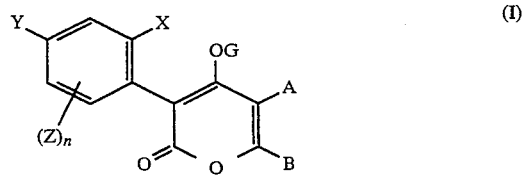

in which the substituents are as defined in the specification. The compounds are useful as pesticides, herbicides and fungicides.

10 Claims, No Drawings

3-ARYL-PYRONE DERIVATIVES

The invention relates to new 3-aryl-pyrone derivatives, to processes for their preparation, and to their use as pesticides.

Certain phenyl-pyrone derivatives which are unsubstituted in the phenyl ring have already been published (cf. A. M. Chirazi, T. Kappe and E. Ziegler, Arch. Pharm. 309, 558 (1976) and K.-H. Boltze and K. Heidenbluth, Chem. Ber. 91, 2849), but a possible utilisation as pesticide has not been indicated for these compounds.

The new substituted 3-aryl-pyrone derivatives of the general formula (I)

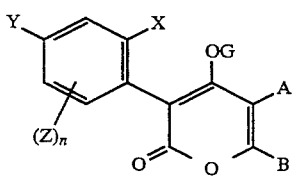

in which
- A represents hydrogen, halogen, optionally substituted radicals from the series comprising alkyl, cycloalkyl, alkenyl, alkinyl, arylalkyl, aryl, hetarylalkyl and hetaryl, or represents the groups —$COR^1$, —$CO_2R^1$, —CN, —$CONR^1R^2$, —$SO_2R^1$ and —$P(O)(OR^1)(OR^2)$, in which
  - $R^1$ and $R^2$ independently of one another represent hydrogen or optionally substituted radicals from the series comprising alkyl, alkenyl, arylalkyl, aryl, hetarylalkyl and hetaryl or
  - $R^1$ and $R^2$ together represent an optionally substituted alkylene group which can be interrupted by one or more hetero atoms;
- B represents hydrogen or optionally substituted radicals from the series comprising alkyl, cycloalkyl, alkenyl, alkinyl, arylalkyl, aryl, hetarylalkyl and hetaryl;
- A and B together form an optionally substituted alkylene or alkenylene group, each of which can be interrupted by, or contain, one or more hetero atoms or hetero groups;
- X represents halogen, alkyl or alkoxy;
- Y represents hydrogen, halogen, alkyl, halogenoalkyl or alkoxy;
- Z represents hydrogen, halogen, alkyl or alkoxy;
- n represents an integer 1, 2 or 3; and
- G represents hydrogen, a metal ion equivalent, an ammonium ion or a group —$COR^3$,

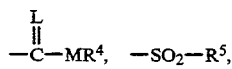

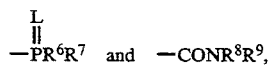

in which
- $R^3$ represents optionally substituted radicals from the series comprising alkyl, alkenyl, alkoxyalkyl, polyalkoxyalkyl, alkylthioalkyl, cycloalkyl which is optionally interrupted by one or more hetero atoms, arylalkyl, aryl, hetarylalkyl, hetaryl, aryloxyalkyl and hetaryloxyalkyl;
- $R^4$ represents optionally substituted radicals from the series comprising alkyl, alkenyl, alkoxyalkyl, polyalkoxyalkyl, aryl and arylalkyl;
- $R^5$, $R^6$ and $R^7$ independently of one another represent optionally substituted radicals from the series comprising alkyl, alkoxy, alkylthio, alkylamino, dialkylamino, alkenylthio, alkinylthio, cycloalkylthio, aryl, aryloxy and arylthio;
- $R^8$ and $R^9$ independently of one another represent hydrogen or optionally substituted radicals from the series comprising alkyl, alkenyl, cycloalkyl, alkoxyalkyl, aryl or arylalkyl, or together form an optionally substituted alkylene group which can be interrupted by one or more hetero atoms or hetero groups;
- L represents oxygen or sulphur; and
- M represents oxygen or sulphur.

Depending on the substituents, the compounds of the general formula (I) can exist in the form of geometric and/or optical isomers or of variously composed mixtures of isomers. The invention claimed embraces the pure isomers as well as the mixtures of isomers, their preparation and use, and the agents containing them. However, the text hereinafter will always mention compounds of the formula (I), for the sake of simplicity, even though this is to be understood as meaning the pure compounds as well as, if appropriate, mixtures containing various proportions of isomeric compounds.

Furthermore, it has been found that the new compounds of the general formula (I) display a very good activity as pesticides, preferably as arthropodicides, nematicides and herbicides, as well as ecto- and endoparasiticides.

Furthermore, it has been found that the new 3-aryl-pyrone derivatives of the general formula (I) are obtained when a) to prepare the compounds in which G represents hydrogen, carbonyl compounds of the general formula (II)

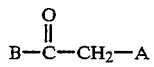

in which
- A and B have the abovementioned meaning, are reacted with acid halides derived from ketene of the general formula (III)

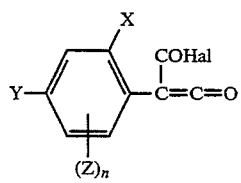

in which
- X, Y, Z and n have the abovementioned meanings and
- Hal represents halogen (preferably chlorine or bromine) in the presence of a diluent and, if appropriate, in the presence of an acid acceptor; and b) to prepare compounds of the general formula (I) in which G represents —$COR^3$, compounds of the general formula (I) in which G represents hydrogen (obtainable by variant a)) are reacted α) with acid halides of the general formula (IV)

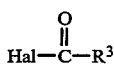  (IV)

in which
R$^3$ has the abovementioned meaning and
Hal represents halogen (preferably chlorine or bromine), or β) with carboxylic anhydrides of the general formula (V)

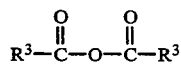  (V)

in which
R$^3$ has the abovementioned meaning, if appropriate in the presence of a diluent and if appropriate in the presence of an acid-binding agent; and c) to prepare compounds of the general formula (I) in which G represents —C(L)—MR$^4$, where L denotes oxygen, compounds of the general formula (I) in which G represents hydrogen (obtainable by variant a)), are reacted with compounds of the general formula (VI)

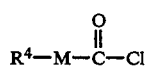  (VI)

in which
R$^4$ and M have the abovementioned meanings, if appropriate in the presence of a diluent and if appropriate in the presence of an acid-binding agent; and d) to prepare compounds of the general formula (I) in which G represents —C(L)—MR$^4$, where L denotes sulphur, compounds of the general formula (I) in which G represents hydrogen (obtainable by variant a)) are reacted α) with compounds of the general formula (VII)

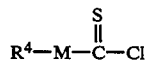  (VII)

in which
R$^4$ and M have the abovementioned meanings, if appropriate in the presence of a diluent and, if appropriate, in the presence of an acid-binding agent, or β) with carbon disulphide (CS$_2$) and subsequently with alkyl halides of the general formula (VIII)

 (VIII)

in which
R$^4$ has the abovementioned meaning and
Hal$^1$ represents halogen (preferably chlorine, bromine and iodine), if appropriate in the presence of a diluent and, if appropriate, in the presence of an acid-binding agent; and e) to prepare compounds of the general formula (I) in which G represents —SO$_2$R$^5$, compounds of the general formula (I) in which G represents hydrogen (obtainable by variant a)), are reacted with sulphonyl chlorides of the general formula (IX)

  (IX)

in which
R$^5$ has the abovementioned meaning, if appropriate in the presence of a diluent and, if appropriate, in the presence of an acid-binding agent; and f) to prepare compounds of the general formula (I) in which G represents —P(L)R$^6$R$^7$, compounds of the general formula (I) in which G represents hydrogen (obtainable by variant a)), are reacted with compounds of the general formula (X)

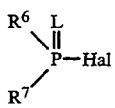  (X)

in which
R$^6$, R$^7$ and L have the abovementioned meanings and
Hal represents halogen (preferably chlorine or bromine), if appropriate in the presence of a diluent and, if appropriate, in the presence of an acid-binding agent; and g) to prepare compounds of the general formula (I) in which G represents a metal ion equivalent or an ammonium ion, compounds of the general formula (I) in which G represents hydrogen (obtainable by variant a)), are reacted with metal hydroxides or amines (preferably mono-, di- or trialkylamines); and h) to prepare compounds of the general formula (I) in which G represents —C(L)NR$^8$R$^9$, compounds of the general formula (I) in which G represents hydrogen (obtainable by variant a)) are reacted α) with compounds of the general formula (XI)

  (XI)

in which
R$^8$ and L have the abovementioned meanings, if appropriate in the presence of a diluent and, if appropriate, in the presence of a catalyst; or β) with compounds of the general formula (XII)

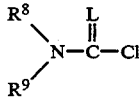  (XII)

in which
R$^8$, R$^9$ and L have the abovementioned meanings, if appropriate in the presence of a diluent and, if appropriate, in the presence of an acid-binding agent.

Alkyl as such or as a component of a different group (for example alkoxy, alkylthio and halogenoalkyl) in the general formulae denotes straight-chain or branched alkyl having advantageously 1 to 20, particularly advantageously 1 to 18 and very particularly advantageously 1 to 16 carbon atoms. Alkyl preferably contains 1 to 8, particularly preferably 1 to 6, and very particularly preferably 1 to 4, carbon atoms, specific mention being made of methyl, ethyl, n- and i-propyl as well as n-, i-, s- and t-butyl.

Cycloalkyl as such or as a component of a different group (for example cycloalkylthio) in the general formulae contains preferably 3 to 10, particularly preferably 3 to 7, and very particularly preferably 3 to 6, carbon atoms, specific mention being made of cyclopropyl, cyclobutyl, cyclopentyl and cyclohexyl. In the case where cycloalkyl is interrupted by one or more hetero atoms or hetero groups, these are identical or different, preferably 1 or 2, hetero atoms or hetero groups. Preferred hetero atoms are oxygen or sulphur, and preferred hetero groups are NH or $NC_1$—$C_4$-alkyl.

Alkenyl and alkinyl as such or as a component of a different group (such as alkenylthio and alkinylthio) in the general formulae denote straight-chain or branched alkenyl and alkinyl having preferably 1 double or triple bond and preferably 2 to 8, in particular 3 to 6, and particularly preferably 3 or 4, carbon atoms, specific mention being made of the allyl and propargyl groups.

Aryl as such or as a component of a different group (such as aryloxy or arylthio) in the general formulae denotes preferably naphthyl and phenyl, particularly preferably phenyl.

Aralkyl in the general formulae preferably denotes naphthylalkyl or phenylalkyl, particularly preferably phenylalkyl. The alkyl moiety is straight-chain or branched and contains preferably 1 to 6, particularly preferably 1 to 4, and very particular preferably 1 or 2, carbon atoms. Specific mention may be made of benzyl and phenylethyl.

Hetaryl as such or as a component of a different group (such as Hetarylalkyl or hetaryloxyalkyl) in the general formulae denotes heteroaromatic 5- to 7-membered rings having preferably 1 to 3, in particular 1 or 2, identical or different hetero atoms. Preferred hetero atoms are oxygen, sulphur or nitrogen. Pyrryl, furyl, thienyl, thiazolyl, pyridyl, pyrazolyl and pyrimidinyl may be mentioned by way of example and as being preferred.

Hetaryl in hetarylalkyl and hetaryloxyalkyl of the general formulae has the meaning mentioned above. The alkyl components are straight-chain or branched and contain preferably 1 to 6, particularly preferably 1 to 4, and very particularly preferably 1 or 2, carbon atoms, specific mention being made of hetarylmethyl and hetaryloxymethyl.

The alkyl moieties in alkylthio, alkoxy, halogenoalkyl, halogenoalkoxy, alkoxyalkyl, alkylthioalkyl, polyalkoxyalkyl, aryloxyalkyl, hetaryloxyalkyl, alkylamino and dialkylamino have the meaning mentioned above in the case of alkyl.

Halogenoalkyl and halogenoalkoxy contain preferably 1 to 8, in particular 1 to 5, and very particularly preferably 1 to 5, identical or different halogen atoms. Halogen atoms are preferably fluorine, chlorine, bromine and/or iodine, in particular fluorine, chlorine and/or bromine, and very particularly preferably fluorine and/or chlorine. Examples which may be mentioned are trifluoromethyl, chloro-difluoromethyl, bromomethyl, 2,2,2-trifluoroethyl and pentafluoroethyl.

In aryloxyalkyl and hetaryloxyalkyl of the general formulae, the aryl, or hetaryl moieties, respectively, have the meanings mentioned above for these radicals.

In alkenylthio, alkinylthio and cycloalkylthio of the general formulae, alkenyl, alkinyl and cycloalkyl have the meanings given above in the case of the particular radicals.

In aryloxy and arylthio of the general formulae, the aryl moieties have the meanings given above for aryl.

The polyalkoxy radicals of the general formulae contain preferably from 2 to 4, in particular 2 to 3, and very particularly preferably 2, alkoxy radicals, the alkyl moieties having the abovementioned meaning.

If two substituents of the general formulae (for example A and B, $R^1$ and $R^2$ as well as $R^8$ and $R^9$) together form an alkylene or alkenylene group, then this group is straight-chain or branched and contains preferably 2 to 7, in particular 2 to 6, and very particularly preferably 2 to 5, carbon atoms. The alkenylene groups contain one or more, preferably 1 or 2, in particular 1, double bond. The alkylene or alkenylene groups can be interrupted by one or more identical or different hetero atoms or hetero groups, such as oxygen, sulphur or nitrogen and —OCO—, or can contain such groups. Examples which may be mentioned are —$(CH_2)_4$—, —$(CH_2)_5$—, —$(CH_2)_2$—O—$(CH_2)_2$— and —$(CH_2)_2$—S—$(CH_2)_2$— or —O—CO—$CH_2$—.

Unless otherwise defined, halogen in the general formulae denotes fluorine, chlorine, bromine and/or iodine, preferably fluorine, chlorine and/or bromine, and very particularly preferably fluorine and/or chlorine.

A metal ion equivalent in the general formulae denotes an equivalent of a metal cation, preferably of the cation of an alkaline earth metal or an alkali metal, in particular of a calcium, magnesium, sodium or potassium cation, very particularly preferably of a calcium, sodium or potassium cation.

An ammonium ion in the general formulae denotes preferably a monoalkyl-, dialkyl- or trialkylammonium ion, the alkyl radicals containing preferably 1 to 6, in particular 1 to 4, and very particularly preferably 1 or 2, carbon atoms. The alkyl radicals can be monosubstituted or polysubstituted, preferably monosubstituted, and mention may be made of hydroxyl or halogen as preferred substituents.

n in the general formulae represents preferably 1 or 2, particularly preferably 1, the substituent Z preferably being in the 6-position of the phenyl ring.

The optionally substituted radicals listed in the general formulae can have one or more, preferably 1 to 3, in particular 1 or 2, identical or different substituents. Substituents which may be mentioned by way example and as being preferred are: alkyl having preferably 1 to 8, in particular 1 to 6, and very particularly preferably 1 to 4, carbon atoms, such as methyl, ethyl, n- and i-propyl and n-, i- and t-butyl; alkoxy having preferably 1 to 8, in particular 1 to 6, and very particularly preferably 1 to 4, carbon atoms, such as methoxy, ethoxy, n- and i-propyloxy and n-, i- and t-butyloxy; alkylthio having preferably 1 to 8, in particular 1 to 6 and very particularly preferably 1 to 4, carbon atoms, such as methylthio, ethylthio, n- and i-propylthio and n-, i- and t-butylthio; halogenoalkyl and halogenoalkoxy having preferably 1 to 8, in particular 1 to 6, and very particularly preferably 1 to 4, carbon atoms and preferably 1 to 7, in particular 1 to 5, and very particularly preferably 1 to 3, carbon atoms, the halogen atoms being identical or different and preferably fluorine, chlorine or bromine, in particular fluorine, such as trifluoromethyl or trifluoromethoxy; hydroxyl; amino; halogen, preferably fluorine, chlorine, bromine and iodine, in particular fluorine, chlorine and bromine; cyano, nitro, phenyl which is optionally substituted by the above-mentioned radicals; alkylcarbonyloxy having preferably 1 to 6, in particular 1 to 4, and very particularly preferably 1 or 2, carbon atoms in the alkyl group, or a heteroaliphatic or heteroaromatic radical such as pyridyl, furyl or tetrahydrofuryl.

A in the general formulae preferably represents hydrogen; halogen, in particular chlorine or fluorine; radicals from the series comprising $C_1$–$C_{10}$-alkyl, $C_3$–$C_{10}$-alkenyl, $C_3$–$C_{10}$-alkinyl and $C_3$–$C_{10}$-cycloalkyl, each of which is optionally substituted by halogen; radicals from the series comprising phenyl, naphthyl, hetaryl, phenyl-$C_1$–$C_6$-alkyl and hetaryl-$C_1$–$C_6$-alkyl, each of which is optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy and/or CN, or represents the groups —$COR^1$, —$CO_2R^1$, —CN, —$CONR^1R^2$, —$SO_2R^1$ and —$P(O)(OR^1)(OR^2)$, in which $R^1$ and $R^2$ independently of one another represent hydrogen, radicals from the series comprising $C_1$–$C_{10}$-alkyl and $C_3$–$C_{10}$-alkenyl, each of which is optionally substituted by halogen; or represent radicals from the series comprising phenyl, naphthyl, hetaryl, phenyl-$C_1$–$C_6$-alkyl and hetaryl-$C_1$–$C_6$-alkyl, each of which is optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy and/or CN; or $R^1$ and $R^2$ together represent a $C_2$–$C_7$-alkylene group which is optionally interrupted by nitrogen, oxygen or sulphur.

A in the general formulae particularly preferably represents hydrogen; halogen; radicals from the series comprising $C_1$–$C_8$-alkyl, $C_3$–$C_8$-alkenyl, $C_3$–$C_8$-alkinyl and $C_3$–$C_8$-cycloalkyl, each of which is optionally substituted by halogen; or represents radicals from the series comprising phenyl, naphthyl, hetaryl, phenyl-$C_1$–$C_4$-alkyl and hetaryl-$C_1$–$C_4$-alkyl, each of which is optionally substituted by halogen, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and/or CN, or represents the groups —$COR^1$, —$CO_2R^1$, —CN, —$CONR^1R^2$, —$SO_2R^1$ and —$P(O)(OR^1)(OR^2)$, in which $R^1$ and $R^2$ independently of one another represent hydrogen, radicals from the series comprising $C_1$–$C_8$-alkyl and $C_3$–$C_8$-alkenyl, which are optionally substituted by halogen; radicals from the series comprising phenyl, hetaryl, phenyl-$C_1$–$C_4$-alkyl and hetaryl-$C_1$–$C_4$-alkyl, which are optionally substituted by halogen, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and/or CN; or $R^1$ and $R^2$ together represent a $C_2$–$C_6$-alkylene group which is optionally interrupted by nitrogen, oxygen or sulphur.

A in the general formulae very particularly preferably represents hydrogen; halogen; radicals from the series comprising $C_1$–$C_6$-alkyl, $C_3$–$C_6$-alkenyl, $C_3$–$C_6$-alkinyl and $C_3$–$C_6$-cycloalkyl, which are optionally substituted by halogen; or represents radicals from the series comprising phenyl, phenyl-$C_1$–$C_2$-alkyl, thienyl, furyl, thiazolyl, pyridyl and pyrazolyl which are optionally substituted by halogen, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and/or CN, or represents the groups —$COR^1$, —$CO_2R^1$, —CN, —$CONR^1R^2$, —$SO_2R^1$ and —$P(O)(OR^1)(OR^2)$, in which $R^1$ and $R^2$ independently of one another represent hydrogen, radicals from the series comprising $C_1$–$C_6$-alkyl and $C_3$–$C_6$-alkenyl, which are optionally substituted by halogen; or represent phenyl which is optionally substituted by halogen, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and/or CN.

In a particularly emphasised embodiment of the present invention, A represents hydrogen, chlorine, fluorine, radicals from the series comprising $C_1$–$C_4$-alkyl, phenyl and benzyl which are optionally substituted by halogen, or A and B together form a $C_3$–$C_5$-alkenyl group (preferably —$CH_2$—$CH(CH_3)$—$(CH_2)_2$—, —$(CH_2)_2$—, —$(CH_2)_4$, —$(CH_2)_5$—, —$CH_2O(CH_2)_2$— or $CH_2$—$S(CH_2)_2$) which is optionally interrupted by oxygen or sulphur.

B in the general formulae preferably represents hydrogen; radicals from the series comprising $C_1$–$C_{10}$-alkyl, $C_3$–$C_{10}$-alkenyl, $C_3$–$C_{10}$-alkinyl and $C_3$–$C_{10}$-cycloalkyl which are optionally substituted by halogen, CN, $C_{1-6}$-alkoxy, $C_{1-6}$-alkylthio, $C_1$–$C_6$-alkylcarbonyloxy or phenyl, or represents radicals from the series comprising phenyl, naphthyl, hetaryl, phenyl-$C_1$–$C_6$-alkyl and hetaryl-$C_1$–$C_6$-alkyl which are optionally substituted by halogen, CN, nitro, $C_1$–$C_8$-alkyl, $C_1$–$C_8$-alkoxy, $C_1$–$C_8$-alkylthio, $C_1$–$C_8$-halogenoalkyl and/or $C_1$–$C_8$-halogenoalkoxy; and A and B in the general formulae together preferably form a $C_2$–$C_7$-alkylene or $C_2$–$C_7$-alkenylene group which can be interrupted by, or contain, nitrogen, sulphur, oxygen or —O—CO— and which is optionally substituted by $C_1$–$C_8$-alkyl, $C_{1-6}$-halogenoalkyl, $C_{1-6}$-alkoxy, $C_{1-6}$-alkylthio and/or halogen.

B in the general formulae particularly preferably represents hydrogen; radicals from the series comprising $C_1$–$C_8$-alkyl, $C_3$–$C_8$-alkenyl, $C_3$–$C_8$-alkinyl and $C_3$–$C_8$-cycloalkyl which are optionally substituted by halogen, CN, $C_{1-4}$-alkyl, $C_{1-4}$-alkylthio, $C_1$–$C_4$-alkylcarbonyloxy or phenyl, or represents radicals from the series comprising phenyl, naphthyl, hetaryl, phenyl-$C_1$–$C_4$-alkyl and hetaryl-$C_1$–$C_4$-alkyl which are optionally substituted by halogen, CN, nitro, $C_1$–$C_6$-alkyl, $C_1$–$C_6$-alkoxy, $C_1$–$C_6$-alkylthio, $C_1$–$C_6$-halogenoalkyl and/or $C_1$–$C_6$-halogenoalkoxy; and A and B in the general formulae together preferably represent a $C_2$–$C_6$-alkylene or $C_2$–$C_6$-alkenylene group which can be interrupted by, or contain, nitrogen, sulphur, oxygen or —O—CO— and which is optionally substituted by $C_1$–$C_4$-alkyl, 1-5-halogeno-$C_{1-4}$-alkyl, $C_{1-4}$-alkoxy and/or halogen.

B in the general formulae very particularly preferably represents hydrogen; radicals from the series comprising $C_1$–$C_6$-alkyl, $C_3$–$C_6$-alkenyl, $C_3$–$C_6$-alkinyl and $C_3$–$C_6$-cycloalkyl which are optionally substituted by CN, methoxy, ethoxy, isopropoxy, methylthio, ethylthio, halogen, $C_1$–$C_4$-alkylcarbonyloxy or phenyl, or represents radicals from the series comprising phenyl, phenyl-$C_1$–$C_2$-alkyl, thienyl, furyl, thiazolyl, pyridyl and pyrazolyl which are optionally substituted by halogen, CN, nitro, $C_1$–$C_4$-alkyl, $C_1$–$C_4$-alkoxy, $C_1$–$C_4$-alkylthio, $C_1$–$C_4$-halogenoalkyl and/or $C_1$–$C_4$-halogenoalkoxy; and A and B in the general formulae together preferably form a $C_2$–$C_5$-alkylene or $C_2$–$C_5$-alkenylene group which can be interrupted by, or contain, sulphur or oxygen and which is optionally substituted by $C_1$–$C_4$-alkyl, $CF_3$, $CCl_3$, $C_2F_5$, $C_2Cl_2F_3$, methoxy, ethoxy and/or halogen.

In a particularly emphasised embodiment of the present invention, B represents hydrogen, $C_1$–$C_4$-alkyl which is optionally substituted by halogen, CN, methoxy or methylthio, or represents radicals from the series comprising phenyl, furyl, thiazolyl and pyridyl which are optionally substituted by halogen, nitro, $C_1$–$C_4$-alkyl and/or $C_1$–$C_4$-alkoxy, and A and B together form the groups —(CH$_2$)$_3$—, —(CH$_2$)$_4$—, —(CH$_2$)$_5$—, —CH$_2$—CH(CH$_3$)(CH$_2$)$_2$—, —CH$_2$O—(CH$_2$)$_2$ and —CH$_2$S(CH$_2$)$_2$—, each of which can be optionally substituted by CF$_3$ or OCH$_3$, such as, for example,

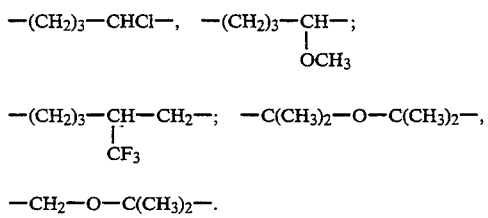

In the general formulae, X preferably represents halogen, $C_1$–$C_6$-alkyl or $C_1$–$C_6$-alkoxy, particularly preferably halogen, $C_1$–$C_4$-alkyl or $C_1$–$C_4$-alkoxy and very particularly preferably fluorine, chlorine, bromine, methyl, ethyl, n- and i-propyl, methoxy or ethoxy, and, in a particularly emphasised embodiment of the invention, methyl.

In the general formulae, Y preferably represents hydrogen, halogen, $C_1$–$C_6$-alkyl, $C_1$–$C_6$-alkoxy or $C_1$–$C_6$-halogenoalkyl, particularly preferably hydrogen, halogen, $C_1$–$C_4$-alkyl, $C_1$–$C_4$-halogenoalkyl or $C_1$–$C_4$-alkoxy, and very particularly preferably hydrogen, fluorine, chlorine, bromine, $C_1$–$C_4$-alkyl or trifluoromethyl, and, in a particularly emphasised embodiment of the invention, methyl.

In the general formulae, Z preferably represents hydrogen, halogen, $C_1$–$C_6$-alkyl or $C_1$–$C_6$-alkoxy, particularly preferably hydrogen, halogen, $C_1$–$C_4$-alkyl or $C_1$–$C_4$-alkoxy and very particularly preferably hydrogen, fluorine, chlorine, bromine, $C_1$–$C_4$-alkyl, methoxy or ethoxy, and, in a particular embodiment of the invention, methyl (preferably in the 6-position of the phenyl ring).

In the general formulae, n represents 1, 2 or 3, preferably 1 or 2, and very particularly preferably 1 (Z preferably being in the 6-position of the phenyl ring).

G in the general formulae preferably represent hydrogen or one of the groups

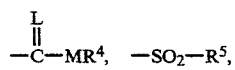

particularly preferably hydrogen,

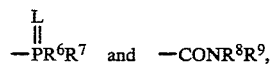

and very particularly preferably hydrogen,

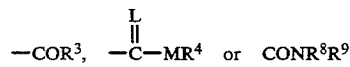

and, in a particularly emphasised embodiment of the invention, hydrogen.

$R^3$ in the general formulae preferably represents radicals from the series comprising $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_1$–$C_8$-alkyl and $C_3$–$C_8$-cycloalkyl which is optionally interrupted by oxygen and/or sulphur, each of these radicals optionally being substituted by halogen; phenyl which is optionally substituted by halogen, nitro, $C_1$–$C_6$-alkyl, $C_1$–$C_6$-alkoxy, $C_1$–$C_6$-halogenoalkyl and/or $C_1$–$C_6$-halogenoalkoxy; phenyl-$C_1$–$C_6$-alkyl which is optionally substituted by halogen, $C_1$–$C_6$-alkyl, $C_1$–$C_6$-alkoxy, $C_1$–$C_6$-halogenoalkyl and/or $C_1$–$C_6$ halogenoalkoxy; hetaryl which is optionally substituted by halogen and/or $C_1$–$C_6$-alkyl; phenoxy-$C_1$–$C_6$-alkyl which is optionally substituted by halogen and/or $C_1$–$C_6$-alkyl, or hetaryloxy-$C_1$–$C_6$-alkyl which is optionally substituted by halogen, amino and/or $C_1$–$C_6$-alkyl.

$R^3$ in the general formulae particularly preferably represents radicals from the series comprising $C_1$–$C_6$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_1$–$C_6$-alkyl and $C_3$–$C_7$-cycloalkyl which is optionally interrupted by oxygen and/or sulphur, each of these radicals optionally being substituted by halogen; phenyl which is optionally substituted by halogen, nitro, $C_1$–$C_4$-alkyl, $C_1$–$C_4$-alkoxy, $C_1$–$C_3$-halogenoalkyl and/or $C_1$–$C_3$-halogenoalkoxy; phenyl-$C_1$–$C_4$-alkyl which is optionally substituted by halogen, $C_1$–$C_4$-alkyl, $C_1$–$C_4$-alkoxy, $C_1$–$C_3$-halogenoalkyl and/or $C_1$–$C_3$-halogenoalkoxy; hetaryl which is optionally substituted by halogen and/or $C_1$–$C_6$-alkyl; phenoxy-$C_1$–$C_5$-alkyl which is optionally substituted by halogen and/or $C_1$–$C_4$-alkyl, or hetaryloxy-$C_1$–$C_5$-alkyl which is optionally substituted by halogen, amino and/or $C_1$–$C_4$-alkyl.

$R^3$ in the general formulae very particularly preferably represents radicals from the series comprising $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_1$–$C_4$-alkyl and $C_3$–$C_6$-cycloalkyl which is optionally interrupted by 1 or 2 oxygen and/or sulphur atoms, each of these radicals optionally being substituted by fluorine and/or chlorine; phenyl which is optionally substituted by fluorine, chlorine, bromine, nitro, $C_1$–$C_3$-alkyl, methoxy, ethoxy, trifluoromethyl and/or trifluoromethoxy; phenyl-$C_1$–$C_3$-alkyl which is optionally substituted by fluorine, chlorine, bromine, $C_1$–$C_3$-alkyl, methoxy, ethoxy, trifluoromethyl and/or trifluoromethoxy; radicals from the series comprising pyridyl, pyrimidyl, thiazolyl and pyrazolyl which are optionally substituted by fluorine, chlorine, bromine, methyl and/or ethyl; phenoxy-$C_1$–$C_4$-alkyl which is optionally substituted by fluorine, chlorine, methyl and/or ethyl, or radicals from the series comprising pyridyloxy-$C_1$–$C_4$-alkyl, pyrimidyloxy-$C_1$–$C_4$-alkyl and thiazolyloxy-$C_1$–$C_4$-alkyl which are optionally substituted by fluorine, chlorine, amino, methyl and/or ethyl.

In a particularly emphasised embodiment of the present invention $R^3$ represents $C_1$–$C_6$-alkyl or $C_1$–$C_6$-alkoxy.

$R^4$ in the general formulae preferably represents radicals from the series comprising $C_1$–$C_{20}$-alkyl, $C_2$–$C_{20}$-alkenyl, $C_1$–$C_8$-alkoxy-$C_1$–$C_8$-alkyl or $C_1$–$C_8$-polyalkoxy-$C_1$–$C_8$-alkyl which are optionally substituted by halogen, or radicals from the series comprising phenyl and benzyl which are optionally substituted by halogen, nitro, $C_1$–$C_6$-alkyl, $C_1$–$C_6$-alkoxy and/or $C_1$–$C_6$-halogenoalkyl.

$R^4$ in the general formulae particularly preferably represents radicals from the series comprising $C_1$–$C_{16}$-alkyl, $C_2$–$C_{16}$-alkenyl, $C_1$–$C_6$-alkoxy-$C_1$–$C_6$-alkyl and $C_1$–$C_6$-polyalkoxy-$C_1$–$C_6$-alkyl which are optionally substituted by halogen, or represents radicals from the series comprising phenyl and benzyl which are optionally substituted by halogen, nitro, $C_1$–$C_4$-alkyl, $C_1$–$C_3$-alkoxy and/or $C_1$–$C_3$-halogenoalkyl.

$R^4$ in the general formulae very particularly preferably represents radicals from the series comprising $C_1$–$C_{14}$-alkyl, $C_2$–$C_{14}$-alkenyl, $C_1$–$C_4$-alkoxy-$C_1$–$C_6$-alkyl or $C_1$–$C_4$-polyalkoxy-$C_1$–$C_6$-alkyl which are optionally substituted by fluorine and/or chlorine, or represents radicals from the series comprising phenyl and benzyl which are optionally substituted by fluorine, chlorine, nitro, $C_1$–$C_3$-alkyl, methoxy, ethoxy and/or trifluoromethyl.

In a particularly emphasised embodiment of the invention, $R^4$ represents $C_1$–$C_6$-alkyl which can be substituted by halogen.

$R^5$, $R^6$ and $R^7$ in the general formulae independently of one another preferably represent radicals from the series comprising $C_1$–$C_8$-alkyl, $C_1$–$C_8$-alkoxy, $C_1$–$C_8$-alkylthio, $C_1$–$C_8$-alkylamino, di-($C_1$–$C_8$)-alkylamino, $C_2$–$C_5$-alkenylthio, $C_2$–$C_5$-alkinylthio. or $C_3$–$C_7$-cycloalkylthio which are optionally substituted by halogen, or represent radicals from the series comprising phenyl, phenyloxy and phenylthio which are optionally substituted by halogen, nitro, cyano, $C_1$–$C_4$-alkoxy, $C_1$–$C_4$-alkylthio, $C_1$–$C_4$-halogenoalkoxy, $C_1$–$C_4$-halogenoalkylthio, $C_1$–$C_4$-alkyl and/or $C_1$–$C_4$-halogenoalkyl.

$R^5$, $R^6$ and $R^7$ in the general formulae independently of one another particularly preferably represent radicals from the series comprising $C_1$–$C_6$-alkyl, $C_1$–$C_6$-alkoxy, $C_1$–$C_6$-alkylthio, $C_1$–$C_6$-alkylamino, di-($C_1$–$C_6$)-alkylamino, $C_2$–$C_4$-alkenylthio, $C_2$–$C_4$-alkinylthio or $C_3$–$C_6$-cycloalkylthio which are optionally substituted by halogen, or represent radicals from the series comprising phenyl, phenyloxy and phenylthio which are optionally substituted by halogen, nitro, cyano, $C_1$–$C_3$-alkoxy, $C_1$–$C_3$-alkylthio, $C_1$–$C_3$-halogenoalkoxy, $C_1$–$C_3$-halogenoalkylthio, $C_1$–$C_3$-alkyl and/or $C_1$–$C_3$-halogenoalkyl.

$R^5$, $R^6$ and $R^7$ in the general formulae independently of one another very particularly preferably represent radicals from the series comprising $C_1$–$C_4$-alkyl, $C_1$–$C_4$-alkoxy, $C_1$–$C_4$-alkylthio, $C_1$–$C_4$-alkylamino or di-($C_1$–$C_4$)-alkylamino which are optionally substituted by fluorine and/or chlorine, or represent radicals from the series comprising phenyl, phenyloxy and phenylthio which are optionally substituted by halogen, nitro, cyano, $C_1$–$C_2$-alkoxy, $C_1$–$C_2$-alkylthio, $C_1$–$C_2$-fluoroalkoxy, $C_1$–$C_2$-chloroalkoxy, $C_1$–$C_2$-fluoroalkylthio, $C_1$–$C_2$-chloroalkylthio and/or $C_1$–$C_3$-alkyl.

In a particularly emphasised embodiment of the invention, $R^5$, $R^6$ and $R^7$ independently of one another represent $C_1$–$C_6$-alkyl which is optionally substituted by halogen.

$R^8$ and $R^9$ in the general formulae independently of one another preferably represent hydrogen, radicals from the series comprising $C_1$–$C_{20}$-alkyl, $C_1$–$C_{20}$-alkoxy, $C_3$–$C_{10}$-cycloalkyl, $C_2$–$C_8$-alkenyl and $C_1$–$C_8$-alkoxy-$C_1$–$C_8$-alkyl which are optionally substituted by halogen, or represent radicals from the series comprising phenyl and benzyl which are optionally substituted by halogen, $C_1$–$C_{20}$-alkyl, $C_1$–$C_{20}$-halogenoalkyl and/or $C_1$–$C_{20}$-alkoxy, or $R^8$ and $R^9$ together form a $C_2$–$C_6$-alkylene group which can be interrupted by oxygen and/or sulphur.

$R^8$ and $R^9$ in the general formulae independently of one another particularly preferably represent hydrogen, radicals from the series comprising $C_1$–$C_{16}$-alkyl, $C_1$–$C_{16}$-alkoxy, $C_3$–$C_{16}$-cycloalkyl, $C_2$–$C_6$-alkenyl and $C_1$–$C_6$-alkoxy-$C_1$–$C_6$-alkyl which are optionally substituted by halogen, or represent radicals from the series comprising phenyl and benzyl which are optionally substituted by halogen, $C_1$–$C_6$-alkyl, $C_1$–$C_6$-halogenoalkyl and/or $C_1$–$C_6$-alkoxy, or $R^8$ and $R^9$ together form a $C_2$–$C_6$-alkylene group which can be interrupted by oxygen and/or sulphur.

$R^8$ and $R^9$ in the general formulae independently of one another very particularly preferably represent hydrogen, radicals from the series comprising $C_1$–$C_{10}$-alkyl, $C_1$–$C_{10}$-alkoxy or $C_1$–$C_{10}$-alkoxy-$C_1$–$C_{10}$-alkyl which are optionally substituted by halogen, or represent radicals from the series comprising phenyl and benzyl which are optionally substituted by halogen, $C_1$–$C_4$-alkyl, $C_1$–$C_4$-halogenoalkyl and/or $C_1$–$C_4$-alkoxy, or $R^8$ and $R^9$ together form a $C_2$–$C_4$-alkylene group which can be interrupted by oxygen and/or sulphur.

In a particularly emphasised embodiment of the invention, $R^8$ and $R^9$ independently of one another represent hydrogen or $C_1$–$C_6$-alkyl which is optionally substituted by halogen.

L in the general formulae preferably (and particularly preferably and very particularly preferably) represents oxygen.

M in the general formulae preferably (and particularly preferably and very particularly preferably) represents oxygen.

The general definitions of radicals or explanations, or the preferred ranges of the definitions of radicals or explanations, which have been mentioned above, can be combined to give any desired combination, that is to say, also between the particular preferred ranges. This applies analogously to the end products and to the precursors and intermediates.

Compounds of the general formula (I) which are preferred according to the invention are those which represent a combination of the meanings mentioned above as being preferred.

Particularly preferred compounds of the general formula (I) according to the invention are those which represent a combination of the meanings mentioned above as being particularly preferred.

Compounds of the general formula (I) which are used in a very particularly preferred manner according to the invention are those which represent a combination of these meanings mentioned above as being very particularly preferred.

The 3-aryl-pyrones required as starting materials for carrying out process variants b), c), d), e), f), g) and h) according to the invention can be obtained by a process variant a).

The acid halides of the formula (IV), carboxylic anhydrides of the formula (V), chloroformic esters or chloroformic thioesters of the formula (VI), chloromonothioformic esters or chlorodithioformic esters of the formula (VII), alkyl halides of the formula (VIII), sulphonyl chlorides of the formula (IX), phosphorus compounds of the formula (X), the compounds of the formulae (XI) and (XII) and the metal hydroxides and amines which are employed, all of which are furthermore required as starting materials for carrying out process variants b), c), d), e), f), g) and h) according to the invention are generally known compounds of organic or inorganic chemistry.

The carbonyl compounds of the formula (II) are also compounds which are generally known in organic chemistry.

Some of the compounds of the formula (III) are known (cf. for example, Org. Prep. Proced. Int., 7(4), 155–8, 1975 and DE 1,945,703). The compounds which were hitherto unknown, however, can be prepared analogously in a simple manner by methods which are known in principle. For example, halogenocarbonyl ketones of the formula (III) are obtained when arylmalonic acids of the formula (XIII)

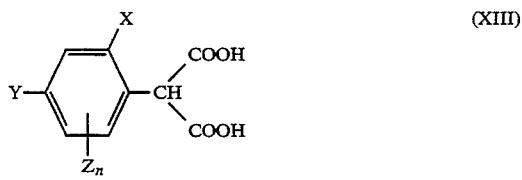

in which

X, Y, Z and n have the abovementioned meaning, are reacted with acid halides such as, for example, thionyl chloride, phosphorus(V) chloride, phosphorus(III) chloride, oxalyl chloride, phosgene or thionyl bromide, if appropriate in the presence of catalysts, such as, for example, diethylformamide, methyl-stearyl formamide or triphenylphosphine.

The arylmalonic acids of the formula (XIII) are generally known compounds of organic chemistry (cf. for example, Organikum [Laboratory Practical in Organic Chemistry], VEB Deutscher Verlag der Wissenschaften, Berlin 1977, p. 517 et seq.).

Diluents which can be employed in process variant a) according to the invention are all inert organic solvents. The following can preferably be used: hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methyl-pyrrolidone.

Acid acceptors which can be used for carrying out process variant a) according to the invention are all customary acid acceptors.

The following can preferably be used: tertiary amines, such as triethylamine, pyridine, diazabicyclooctane (DABCO), diazabicycloundecane (DBU), diazabicyclononene (DBN), Hünig base and N,N-dimethyl-aniline.

When carrying out process variant a) according to the invention, the reaction temperatures can be varied within a substantial range. It is expedient to carry out process variant a) at temperatures between 0° C. and 250° C. preferably between 50° C. and 220° C.

Process variant a) according to the invention is expediently carried out under atmospheric pressure.

When carrying out process variant a) according to the invention, the reactants of the formulae (II) and (III) and, if appropriate, the acid acceptors are expediently applied in approximately equimolar amounts. However, it is also possible to use one component or the other in a larger excess (up to 5 mol).

If the acid halides are used, then diluents which can be employed in process variant b) α) according to the invention are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylates such as ethyl acetate, and also strongly polar solvents such as dimethyl sulphoxide and sulpholane. If the acid halide is sufficiently stable to hydrolysis, the reaction can also be carried out in the presence of water.

If the corresponding carboxylic halides are used, then acid-binding agents which are suitable for the reaction by process variant b) α) according to the invention are all customary acid acceptors. The following can preferably be used: triethylamine, pyridine, diazabicyclooctane (DABCO), diazabicycloundecane (DBU), diazabicyclononene (DBN), Hünig base and N,N-dimethyl-aniline, furthermore alkaline earth metal oxides such as magnesium oxide and calcium oxide, moreover alkali metal carbonates and alkaline earth metal carbonates such as sodiumcarbonate, potassium carbonate and calcium carbonate, and also alkali metal hydroxides such as sodium hydroxide and potassium hydroxide.

When carrying out process variant b) α) according to the invention, the reaction temperatures can also be varied within a substantial range. Process variant b) α) according to the invention is expediently carried out at temperatures between −20° C. and +150° C., preferably between 0° C. and 100° C.

When carrying out process variant b) α) according to the invention, the starting materials of the formula (I) and the carboxylic acid halide of the formula (V) are preferably used in approximately equivalent amounts. However, it is also possible to employ the carboxylic acid halide in a larger excess (up to 5 mol). Working-up is carried out by customary methods.

If, in process variant b) β) according to the invention, carboxylic anhydrides are used as reactants of the formula (V), then preferred diluents which can be used are those which are also preferably suitable when acid halides are used. Apart from these, a carboxylic anhydride employed in excess can also act simultaneously as the diluent. Equally, the acid acceptors which can be employed are those acid acceptors indicated for process variant b) α).

When carboxylic anhydrides are used, the reaction temperatures for process variant b) β) according to the invention can also be varied within a substantial range. It is expedient to carry out process variant b) β) at temperatures between −20° C. and +150° C., preferably between 0° C. and 100° C.

When carrying out the process according to the invention, the starting materials of the formula (I) and the carboxylic anhydride of the formula (V) are preferably used in approximately equivalent amounts. However, it is also possible to employ the carboxylic anhydride in a larger excess (up to 5 mol). Working-up is carried out by customary methods.

Expediently, a procedure is followed in which the diluent and an excess of carboxylic anhydride as well as the carboxylic acid which forms are removed by distillation or by washing with an organic solvent or with water.

If, in process variant c), the corresponding chloroformic esters or chloroformic thioesters, then acid-binding agents which are suitable for the reaction are all customary acids acceptors.

The following can preferably be used: tertiary amines such as triethylamine, pyridine, 1,4-diazabicyclo[2.2.2]octane (DABCO), 1,8 diazabicyclo[5.4.0]undecane-7-ene (DBU), DBA, Hünig base and N,N-dimethyl-aniline, furthermore alkaline earth metal oxides such as magnesium oxide and calcium oxide, moreover alkali metal carbonates and alkaline earth metal carbonates such as sodium carbonate, potassiumcarbonate and calciumcarbonate, and also alkali metal hydroxides such as sodium hydroxide or potassium hydroxide.

When the chloroformic esters, or chloroformic thioesters are used, then diluents which can be employed in process variant c) according to the invention are all solvents which are inert to these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers such as diethyl ether, tetrahydrofuran and dioxane, moreover carboxylates, such as ethyl acetate, and also strongly polar solvents, such as dimethyl sulphoxide and sulpholane.

When the chloroformic esters, or chloroformic thioesters are used as carboxylic acid derivatives of the formula (VI), the reaction temperatures for carrying out process variant c) according to the invention can be varied within a substantial range. If process variant c) is carried out in the presence of a diluent and of an acid-binding agent, then the reaction temperatures are generally between $-20°$ C. and $+100°$ C., preferably between $0°$ C. and $50°$ C.

Process variant c) according to the invention is expediently carried out under atmospheric pressure.

When carrying out process variant c) according to the invention, the starting materials of the formula (I) and the corresponding chloroformic ester, or chloroformic thioester, of the formula (VI) are preferably used in approximately equivalent amounts. However, it is also possible to employ one component or the other in a larger excess (up to 2 mol). Working-up is then carried out by customary methods. Expediently, a method is followed in which precipitated salts are removed and the reaction mixture which remains is concentrated by stripping off the diluent.

In process variant d) α), approximately 1 mol of chloromonothioformic ester, or chlorodithioformic ester, of the formula (VII) is reacted per mole of starting compound of the formula (I) at $0°$ to $120°$ C., preferably at $20°$ to $60°$ C.

Suitable diluents which may be added are all inert polar organic solvents such as ethers, amides, alcohols, sulphones and sulphoxides.

Dimethyl sulphoxide, tetrahydrofuran, dimethylformamide or dimethyl sulphide are preferably employed.

If, in a preferred embodiment, the enolate salt of the compound (I) is synthesized by adding strong deprotonating agents such as, for example, sodium hydride or potassium tertiary butylate, further additives of acid-binding agents can be dispensed with.

If acid-binding agents are employed, then customary inorganic or organic bases are suitable, examples which may be mentioned being sodium hydroxide, sodium carbonate, potassium carbonate, pyridine and triethylamine.

The reaction can be carried out under atmospheric pressure or under increased pressure, preferably under atmospheric pressure. Working-up is carried out by customary methods.

In process variant d) β), an equimolar amount, or an excess, of carbon disulphide is added per mole of starting compound of the formula (I). Process variant d) β) is preferably carried out at temperatures from $0°$ to $50°$ C., in particular at $20°$ to $30°$ C.

Frequently, it is expedient to first prepare the corresponding salt from the compound of the formula (I) by adding a deprotonating agent (such as, for example, potassium tertiary butylate or sodium hydride). The compound (I) is reacted with carbon disulphide until the formation of the intermediate is complete, for example after stirring at room temperature for several hours.

The further reaction with the alkyl halide of the formula (VIII) is preferably carried out at $0°$ to $70°$ C., in particular at $20°$ to $50°$ C. At least an equimolar amount of alkyl halide is employed.

Process variant d) β) is carried out under atmospheric pressure or under increased pressure, preferably under atmospheric pressure.

Again, working-up is carried out by customary methods.

In process variant e), approximately 1 mol of sulphonyl chloride (IX) is reacted per mole of starting compound of the formula (I) at $0°$ to $150°$ C., preferably at $20°$ to $70°$ C.

Suitable diluents which may be added are all inert polar organic solvents such as ethers, amides, nitriles, alcohols, sulphones, sulphoxides or halogenated hydrocarbons such as methylene chloride.

Dimethyl sulphoxide, tetrahydrofuran and dimethylformamide are preferably employed.

If, in a preferred embodiment, the enolate salt of the compound (I) is synthesized by adding strong deprotonating agents (such as, for example, sodium hydride or potassiumtertiary butylate), a further addition of acid-binding agents can be dispensed with.

If acid-binding agents are employed, then customary inorganic or organic bases are suitable, sodium hydroxide, sodium carbonate, potassium carbonate, pyridine and triethylamine being mentioned by way of example.

The reaction can be carried out under atmospheric pressure or under increased pressure, preferably under atmospheric pressure. Working-up is carried out by customary methods.

If appropriate, process variant e) can be carried out under phase transfer conditions (W. J. Spillane et al.; J. Chem. Soc., Perkin Trans I, (3) 677–9 (1982)). In this case, 0.3 to 1.5 mol of sulphonyl chloride (IX), preferably 0.5 mol, are reacted per mole of starting compound of the formula (I) at $0°$ to $150°$ C. preferably at $20°$ to $70°$ C.

Suitable phase transfer catalysts which can be used are all quaternary ammonium salts, preferably tetraoctylammonium bromide and benzyltriethylammonium chloride. Organic solvents which can be used in this case are all unpolar inert solvents, preferably benzene and toluene being employed.

In process variant f), 1 to 2, preferably 1 to 1.3 mol of the phosphorus compound of the formula (X) are reacted per mole of the compound (I) at temperatures between −40° C. and 150° C., preferably between −10° and 110° C.

Diluents which may be added are all inert, polar organic solvents such as ethers, amides, nitriles, alcohols, sulphides, sulphones, sulphoxides and the like.

Acetonitrile, dimethyl sulphoxide, tetrahydrofuran and dimethylformamide are preferably employed.

Suitable acid-binding agents which may be added are customary inorganic or organic bases such as hydroxides or carbonates. Examples which may be mentioned are sodium hydroxide, sodium carbonate, potassium carbonate and pyridine.

The reaction can be carried out under atmospheric pressure or under increased pressure, preferably under atmospheric pressure. Working-up is carried out by customary methods of organic chemistry. The end products obtained are purified preferably by crystallisation, by means of chromatography or by so-called "incipient distillation", that is to say removal of the volatile components in vacuo.

Process variant g) is characterised in that compounds of the formula (I) are reacted with metal hydroxides or amines.

Diluents which can be used in the process according to the invention are preferably ethers such as tetrahydrofuran, dioxane, diethyl ether, or else alcohols such as methanol, ethanol and isopropanol, but also water. The process is preferably carried out under atmospheric pressure. The reaction temperatures are generally between −20° C. and 100° C., preferably between 0° C. and 50° C.

When carrying out process variant g) according to the invention, the starting materials are generally used in approximately equimolar amounts. However, it is also possible to employ one component or the other in a larger excess (up to 2 mol). Expediently, a procedure is followed in which the reaction mixture is concentrated by stripping off the diluent.

In process variant h) β), approximately 1 mol of isocyanate of the formula (XI) is reacted per mole of starting compound of the formula (I) at 0° to 100° C., preferably at 20° to 50° C.

Suitable diluents which may be added are all inert organic solvents such as ethers, amides, nitriles, sulphones and sulphoxides.

If appropriate, catalysts can be added to accelerate the reaction. Catalysts which can be employed very advantageously are organotin compounds, such as, for example, dibutyltin dilaurate. Process variant h) α) is preferably carried out under atmospheric pressure.

In process variant h) β), approximately 1 mol of carbamoyl chloride or thiocarbamoyl chloride, of the formula (XII), is reacted per mole of starting compound of the formula (I) at 0° to 150°C., preferably at 20° to 70° C.

Suitable diluents which may be added are all inert polar organic solvents such as ethers, amides, alcohols, sulphones or sulphoxides.

Dimethyl sulphoxide, tetrahydrofuran and dimethylformamide are preferably employed.

If, in a preferred embodiment, the enolate salt of the compound (I) is synthesized by adding strong deprotonating agents (such as, for example, sodium hydride or potassium tertiary butylate, a further addition of acid-binding agents can be dispensed with.

If acid-binding agents are employed, then customary inorganic or organic bases are suitable, sodium hydroxide, sodium carbonate, potassium carbonate and pyridine being mentioned by way of example.

The reaction can be carried out under atmospheric pressure or under increased pressure, preferably under atmospheric pressure. Working-up is carried out by customary methods. The compounds of the formula (I) according to the invention can be employed for combating pests. Pests are undesired animal pests, in particular insects, mites and nematodes, which are harmful to plants or higher animals. However, pests also include undesired plants.

The active compounds according to the invention are suitable for combating animal pests, preferably arthropods, in particular insects, arachnids and nematodes, which are encountered in agriculture, in forests, in protection of stored products and materials, and in the hygiene field, and they are well tolerated by plants and have favourable toxicity to warm-blooded animals. They are active against normally sensitive and resistant species and against all or some stages of development.

The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosi-*

*phum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichordorus spp.

Besides, the active compounds of the formula (I) according to the invention also have a good fungicidal activity and can be employed for combating plant diseases such as, for example, the causative organism of a rice blast disease (*Pyricularia oryzae*).

For use as insecticides, acaricides and nematicides, the active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The compounds according to the invention are also particularly suitable for the treatment of vegetative and generative propagation material such as, for example, seed of cereals, maize, vegetables and the like, or onions, cuttings and the like.

When used against hygiene pests and pests of stored products, the active compounds are distinguished by an excellent residual action on wood and clay as well as a good stability to alkali on limed substrates.

The active compounds according to the invention can also be used as herbicides, preferably as defoliants, desiccants, agents for destroying broad-leaved plants and, in particular, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the qenera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating monocotyledon weeds in dicotyledon cultures by the pre- and post-emergence methods.

The active compounds according to the invention, as such or in the form of their formulations, can also be used for combating weeds in the form of a mixture with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferablybetween 50 g and 5 kg per hectare.

To prepare the pesticides the active compounds according to the invention can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

Depending on their particular physical and/or chemical properties, the active compounds can be converted into customary formulations, such as solutions, emulsions, suspensions, powders, foams,.pastes, granules, aerosols, natural and synthetic substances which are impregnated with active compound, very fine capsules in polymeric substances, and in coating compositions for seed, and furthermore in formulations used with burning equipment, such as fumigating cartridges, fumigating cans, fumigating coils and the like, as well as ULV cold mist and warm mist formulations. These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The agents according to the invention preferably contain, besides at least one compound of the general formula (I) and, if appropriate, besides considerable extenders and auxiliaries, at least one surface-active substance.

The active compounds have a favourable toxicity to warm-blooded animals and are also suitable for combating animal pests (ecto- and endoparasites) such as arthropods, preferably insects and arachnids (ectoparasites), Cestodes, Trematodes, Nematodes and Acantocephala (endoparasites) which are encountered in animal keeping and livestock breeding in domestic animals and productive livestock as well as in zoo animals, laboratory animals, experimental animals and pets. They are active against all or individual development stages of the pests and against resistant and normally sensitive species of the pests.

By combating the animal pests, it is intended to prevent disease and their transmission, deaths and reductions in performance (for example in the production of meat, milk, wool, hides and eggs), so that, by using the active compounds, more economical and simpler animal keeping is possible, or, in certain areas, made possible in the first place.

The pests include:

From the order of the Anoplura, for example, Haematopinus spp., Linognathus spp., Solenopotes spp., Pediculus spp., Pthirus spp.;

From the order of the Mallophaga, for example, Trimenopon spp., Menopon spp., Eomenacanthus spp., Menacathus spp., Trichodectes spp., Felicola spp., Damalinea spp., Bovicola spp.;

From the order of the Diptera, for example, Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.

From the order of the Siphonaptera, for example, Ctenocephalides spp., Echidnophaga spp., Ceratophyllus spp.

From the order of the Metastigmata, for example, Hyalomma spp., Rhipicephalus spp., Boophilus spp., Amblyomma spp., Haemophysalis spp., Dermacentor spp., Ixodes spp., Argas spp., Ornithodorus spp., Otobius spp.;

From the order of the Mesastigmata, for example, Dermanyssus spp., Ornithonyssus spp., Pneumonyssus spp.

From the order of the Prostigmata, for example, Cheyletiella spp., Psorergates spp., Myobia spp., Demodex spp., Neotrombicula spp.;

From the order of Astigmata, for example, Acarus spp., Myocoptes spp., Psoroptes spp., Chorioptes spp., Otodectes spp., Sarcoptes spp., Notoedres spp., Knemidocoptes spp., Neoknemidocoptes spp., Lytodites spp., Laminosioptes spp.

The endo parasites include:

From the order of the Pseudophyllidea, for example Diphyllobothrium spp., Spirometra spp., Schistocephalus spp., Ligula spp., Bothridium spp., Diphlogonoporus spp.

From the order of the Cyclophyllidea, for example Mesocestoides spp., Anoplocephala spp., Paranoplocephala spp., Moniezia spp., Thysanosomsa Spp,, Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example Gyrodactylus spp., Dactylogyrus spp., Polystoma spp.

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridiumspp., Brachylaima spp., Echinostoma spp., Echinoparyphium spp., Echinochasmus spp., Hypoderaeum spp., Fasciola spp., Fasciolides spp., Fasciolopsis spp., Cyclocoelumspp., Typhlocoelumspp., Paramphistomumspp., Calicophoron spp., Cotylophoron spp., Gigantocotyle spp., Fischoederius spp. Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.

From the order of the Enoplida, for example Trichuris spp., Capillaria spp., Trichomosoides spp., Trichinella spp.

From the order of the Rhabditia, for example Micronema spp., Strongyloides spp.

From the order of the Strongylida, for example Strongylus spp., Triodontophorus spp., Oesophagodontus spp., Trichonema spp., Gyalocephalus spp., Cylindropharynx spp., Poteriostomum spp., Cyclococerus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example Oxyuris spp., Enterobius spp., Passalurus spp., Syphacia spp., Aspiculuris spp., Heterakis spp.

From the order of the Spirurida, for example Gnathostoma spp., Physaloptera spp., Thelazia spp., Gongylonema spp., Habronema spp., Parabronema spp., Draschia spp., Dracunculus spp.

From the order of the Filariida, for example Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example Filicollis spp., Moniliformis spp., Macracanthorhynchus spp., Prosthenorchis spp.

The reproductive livestock and breeding animals include mammals, such as, for example, cattle, horses, sheep, pigs, goats, camels, water buffaloes, donkeys, rabbits, fallow deer or reindeer, fur-bearing animals, such as, for example, minks, chinchilla or racoon, birds, such as, for example chickens, geese, turkeys or ducks, freshwater fish and sea fish, such as, for example, trout, carp and eels, reptiles and insects, such as, for example, honeybee and silk worm.

The laboratory and experimental animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the environment or with the aid of shaped articles containing the active compound, such as, for example, strips, plates, tapes, neck bands, ear tags, limb bands or marking devices.

Enteral administration of the active compound is effected for example orally in the form of powders, tablets, suppositories, capsules, pastes, drinks, granules, drenches, boli, medicated feed or drinking water. Dermal administration is effected, for example, in the form of dipping, spraying, bathing, washing, pouring-on and spotting-on and dusting. Parenteral administration is effected, for example, in the form of injection (intramuscular, subcutaneous, intravenous or intraperitoneal) or by implants.

The following are suitable preparations:

Solutions, such as solutions for injection, oral solutions, concentrates for oral administration after dilution, solutions for use on the skin or in body cavities, pour-on and spot-on formulations, gels;

Emulsions and suspension for oral or dermal administration and for injection; semi-solid preparations;

Formulations in which the active compound is incorporated in a cream base or in an oil-in-water or water-in-oil emulsion base;

Solid preparations, such as powders, premixes or concentrates, granules, pellets, tablets, boli, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, by adding additives, such as solubilisers, acids, bases, buffer salts, antioxidants, or preservatives. The solutions are sterile-filtered and decanted into containers.

The following may be mentioned as solvents: physiologically acceptable solvents, such as water, alcohols, such as ethanol, butanol, benzyl alcohol, glycerol, hydrocarbons, propylene glycol, polyethylene glycols and N-methyl-pyrrolidone, and their mixtures.

If appropriate, the active compounds can also be dissolved in physiologically acceptable vegetable or synthetic oils which are suitable for injection.

The following may be mentioned as solubilisers: solvents which facilitate the dissolution of the active compound in the main solvent or which prevent precipitation of the active compound. Examples of solubilisers are polyvinylpyrrolidone, polyoxyethylated castor oil and polyoxyethylated sorbitan esters.

The following are preservatives: benzyl alcohol, trichlorobutanol, p-hydroxybenzoates or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on. These solutions are prepared as described above in the case of the solutions for injection.

It may be advantageous to add thickeners in the preparation process. The following are thickeners: inorganic thickeners, such as bentonites, colloidal silica, aluminium monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described in the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other auxiliaries, such as colorants, resorption accelerators, antioxidants, light stabilizers or tackifiers, are added.

The following may be mentioned as solvents: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methyl-pyrrolidone or 2,2-dimethyl-4-oxymethylene1,3-dioxolane.

Colorants are all colorants which can be in dissolved or suspended form and which are released for use in animals.

Examples of resorption accelerators are DMSO, spreading oils, such as isopropyl myristate, dipropylene glycol pelargonate, silicone oils, fatty acid esters, triglycerides or fatty alcohols.

The following are antioxidants: sulphites or metabisulphites, such as potassium metabisulphite, ascorbic acid, butylhydroxytoluene, butylhydroxyanisole or tocopherol.

An example of a light stabiliser is novantisolic acid. Tackifiers are, for example, cellulose derivatives, starch derivatives, polyacrylates or natural polymers such as alginates, or gelatine.

Emulsions can be administered orally, dermally or as injections.

Emulsions are either the water-in-oil type or the oil-in-water type.

They are prepared by dissolving the active compound either in the hydrophobic or in the hydrophilic phase and homogenising this phase with the solvent of the other phase, with the aid of suitable emulsifiers and, if appropriate, other auxiliaries, such as colorants, resorption accelerators, preservatives, antioxidants, light stabilisers, and viscosity-increasing substances.

The following may be mentioned as the hydrophobic phase (oils): paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryladipate, hexyl laurate, dipropylene glycol pelargonate, esters of a branched fatty acid having a medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

The following may be mentioned as the hydrophilic phase: water, alcohols, such as, for example, propylene glycol, glycerol, sorbitol and their mixtures.

The following may be mentioned as emulsifiers: nonionic surfactants, for example polyoxyethylated castor oil, polyoxyethylated sorbitan monooleate, sorbitan monostearate, glycerol monostearate, polyoxyethyl stearate or alkylphenol polyglycol ethers;

ampholytic surfactants, such as disodium N-lauryl-$\beta$-aminodipropionate or lecithin;

anionic surfactants, such as Na lauryl sulphate, fatty alcohol ether sulphates, and the monoethanolamine salt of mono/dialkyl polyglycol ether orthophosphoric ester;

cationic surfactants, such as cetyltrimethylammonium chloride.

The following may be mentioned as other auxiliaries: substances which increase the viscosity and stabilise the emulsion, such as carboxymethylcellulose, methylcellulose and other cellulose and starch derivatives, polyacrylates, alginates, gelatin, gum arabic, polyvinylpyrrolidone, polyvinyl alcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, resorption accelerators, preservatives, antioxidants andlight stabilisers.

Liquid excipients which may be mentioned are all homogenous solvents and solvent mixtures.

Wetting agents (dispersants) which may be mentioned are the wetting agents indicated further above.

Other auxiliaries which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Excipients which may be mentioned are all physiologically acceptable solid inert substances. Suitable for this purpose are inorganic and organic substances. Inorganic substances are, for example, common salt, carbonates, such as calcium carbonate, hydrogencarbonates, aluminium oxides, silicas, clays, precipitated or colloidal silicon dioxide, and phosphates.

Organic substances are, for example, sugars, cellulose, foodstuffs and animal feeds, such as powdered milk, carcass meals, cereal meals, coarse cereal meals and starches.

Auxiliaries are preservatives, antioxidants and colorants which have already been mentioned further above.

Other suitable auxiliaries are lubricants and gliding agents, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

The present invention therefore also relates to the compounds of the general formula (I) for use as ecto- and endoparasiticides, and to the use of the compounds of the general formula (I) for the preparation of an agent for combating ecto- and endoparasites.

In the preparations, the active compounds can also be present in mixtures with synergists or other active compounds which are active against pathogenic endoparasites. Examples of such active compounds are L-2,3,5,6-tetrahydro-6-phenyl-imidazothiazole, benzimidazole carbamates, praziquantel, pyrantel or febantel.

Ready-to-use preparations contain the active compound in concentrations of 10 ppm to 20 percent by weight, preferably from 0.1 to 10 percent by weight.

Preparations which are diluted before use contain the active compound in concentrations of 0.5 to 90 percent by weight, preferably from 5 to 50 percent by weight.

In general, to achieve effective results, it has proved advantageous to administer amounts of about 1 to about 100 mg of active compound per kg of body weight per day.

The compounds according to the invention are preferably employed as arthropodicides and herbicides in the sectors plant protection, domestic premises and hygiene, and in the protection of stored products, very particularly preferably for plant protection.

Unless otherwise indicated, all percentages are percent by weight.

The preparation of the compounds of the general formula (I) according to the invention will be illustrated by the following preparation examples, and the biological activity will be illustrated by the following biological examples.

EXAMPLE 1

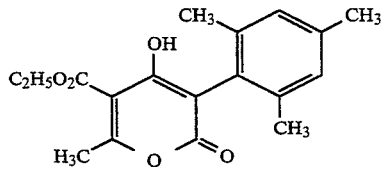

13.0 g (0.1 mol) of ethyl acetate are added dropwise, with the exclusion of moisture, at 20° C. to 22.2 g (0.1 mol) of chlorocarbonyl-2,4,6-trimethylphenylketene in 200 ml of absolute toluene, and the mixture is subsequently refluxed for 3 hours. The toluene phase is washed with water, the solvent is distilled off, and the residue is chromatographed on 1 kg of silicone gel (35 to 70 μm) using toluene/acetone (20:1 parts by volume). 17.9 g of 5-ethoxy-4-hydroxy-6-methyl-3-(2,4,6-trimethylphenyl)pyrone are obtained (yield: 57% of theory). $^1$H NMR (CDCl$_3$, TMS as internal standard): δ=2.23 (s, 3H), 2.70 (s, 3H), 6.90 (s, 2H) and 11.75 (s, 1H).

EXAMPLE 2

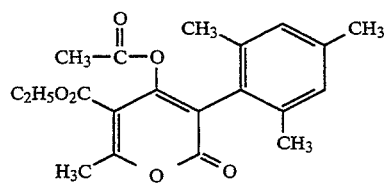

1.0 g (10 mmol) of triethylamine and then 0.8 g (10 mmol) of acetyl chloride are added dropwise at 0° C. to 3.2 g (10 mmol) of 5-ethoxycarbonyl-4-hydroxy-6-methyl-3-(2,4,6-trimethylphenyl)pyrone in ml of ethyl acetate. The mixture is stirred for 20 hours at 20° C. and filtered, the organic phase is washed with semi-concentrated sodium chloride solution and dried over sodium sulphate and the solvent is evaporated in vacuo. The residue is chromatographed on silica gel (35–70 μm) using toluene/acetone (40:1 parts by volume). 2.9 g of 4-acetoxy-5-ethoxycarbonyl-6-methyl-3-(2,4,6-trimethylphenyl)pyrone are obtained (yield: 81% of theory). M.p.=107° to 109° C.

EXAMPLE 3

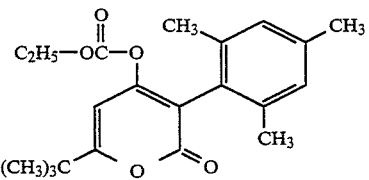

2.0 g (20 mmol) of triethylamine and subsequently 2.2 g (20 mmol) of ethyl chloroformate in 20 ml of ethyl acetate are added dropwise at 0° C. to 5.7 g (20 mmol) of 4-hydroxy-6-tert.-butyl-3-(2,4,6-trimethylphenyl)pyrone in 50 ml of ethyl acetate. The mixture is stirred for 20 hours at 20° C. and filtered, the organic phase is washed with semi-concentrated sodium chloride solution and dried over sodium sulphate, and the solvent is evaporated in vacuo. The residue is chromatographed on silica gel (35–70 μm) using toluene/acetone (20:1 parts by volume). 6.0 g of 4-ethoxycarbonyloxy-6-tert.-butyl-3-(2,4,6-trimethylphenyl)pyrone are obtained (yield: 84% of theory). M.p.=92°–94° C.

The 3-aryl-pyrone derivatives of the general formula (I) whose formulae are listed in Tables 1 to 3 below are obtained analogously to the Preparation Examples and following the general information on the description of the preparation.

TABLE 1

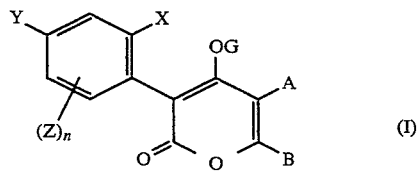

| Example No. | X | Y | (Z)$_n$ | A | B | G | M.p.(°C.) $^1$H NMR(CDCl$_3$) [ppm], δ: |
|---|---|---|---|---|---|---|---|
| 4 | CH$_3$ | H | 6-CH$_3$ | CO$_2$C$_2$H$_5$ | CH$_3$ | H | 147–149 |
| 5 | CH$_3$ | CH$_3$ | 6-CH$_3$ | CO$_2$H | CH$_3$ | H | 240–242 |
| 6 | CH$_3$ | CH$_3$ | 6-CH$_3$ | CO$_2$-i-C$_4$H$_9$ | CH$_3$ | H | 1.04(d, J=3Hz, 6H) 4.18(d, J=3Hz, 2H) 6.89(s, 2H) |

TABLE 1-continued $$\text{(I)}$$

| Example No. | X | Y | (Z)$_n$ | A | B | G | M.p.(°C.) $^1$H NMR(CDCl$_3$) [ppm], δ: |
|---|---|---|---|---|---|---|---|
| 7 | CH$_3$ | CH$_3$ | 6-CH$_3$ | CO$_2$CH$_2$CH=CH$_2$ | CH$_3$ | H | 2.70(s, 3H), 4.84 (d, J=3Hz), 6.90 (s, 2H) and 11.65 (s, 1H) |
| 8 | CH$_3$ | CH$_3$ | 6-CH$_3$ | CO$_2$CH$_2$C$_6$H$_5$ | CH$_3$ | H | 2.48(s, 3H), 5.43 (s, 2H), 6.88(s, 2H) and 11.65(s, 1H) (D-DMF) |
| 9 | CH$_3$ | CH$_3$ | 6-CH$_3$ | CO$_2$CH$_2$-(tetrahydrofuran-2-yl) | CH$_3$ | H | 2.73(s, 3H), 3.73–4.43 (m, 4H), 6.85 (s, 2H) |
| 10 | CH$_3$ | CH$_3$ | 6-CH$_3$ | CN | C$_6$H$_5$ | H | 244–246 |
| 11 | CH$_3$ | CH$_3$ | 6-CH$_3$ | CN | C(CH$_3$)$_3$ | H | 144–146 |
| 12 | CH$_3$ | CH$_3$ | 6-CH$_3$ | CN | 3,4-(CH$_3$O)$_2$—C$_6$H$_3$ | H | 250–253 |
| 13 | CH$_3$ | CH$_3$ | 6-CH$_3$ | CN | 2-Cl—C$_6$H$_4$ | H | 272–274 |
| 14 | CH$_3$ | CH$_3$ | 6-CH$_3$ | CO$_2$C$_2$H$_5$ | 2-F—C$_6$H$_4$ | H | 181–183 |
| 15 | CH$_3$ | CH$_3$ | 6-CH$_3$ | CO$_2$C$_2$H$_5$ | 4-NO$_2$—C$_6$H$_4$ | H | 194–197 |
| 16 | CH$_3$ | CH$_3$ | 6-CH$_3$ | CO$_2$C$_2$H$_5$ | CH(CH$_3$)$_2$ | H | 1.20(d, J=3Hz, 6H) 3.93(q, J=3Hz, 1H) 6.91(s, 2H) |
| 17 | CH$_3$ | CH$_3$ | 6-CH$_3$ | CO$_2$C$_2$H$_5$ | C$_2$H$_5$ | H | 127–130 |
| 18 | CH$_3$ | CH$_3$ | 6-CH$_3$ | CON(morpholino) | CH$_3$ | H | 2.10(s, 6H), 2.28 (s, 3H), 2.31(s, 3H) 3,45–3.80 (m, 8H) |
| 19 | CH$_3$ | CH$_3$ | 6-CH$_3$ | CONH-3-Br—C$_6$H$_4$ | CH$_3$ | H | 120–122 |
| 20 | CH$_3$ | CH$_3$ | 6-CH$_3$ | CON(piperidino) | CH$_3$ | H | 193–195 |
| 21 | CH$_3$ | CH$_3$ | 6-CH$_3$ | SO$_2$C$_6$H$_5$ | CH$_3$ | H | 2.10(s, 6H), 2.29 (s, 3H), 2.60(s, 3H) 7.12–7.92(m, 5H) |
| 22 | CH$_3$ | CH$_3$ | 6-CH$_3$ | SO$_2$CH$_3$ | CH$_3$ | H | 2.11(s, 6H), 2.29 (s, 3H), 2.74(s, 3H), 3.25(s, 3H) |
| 23 | CH$_3$ | CH$_3$ | 6-CH$_3$ | SO$_2$-4-Cl—C$_6$H$_4$ | CH$_3$ | H | 199–202 |
| 24 | CH$_3$ | CH$_3$ | 6-CH$_3$ | P(O)(OCH$_3$)$_2$ | CH$_3$ | H | 149–152 |
| 25 | CH$_3$ | CH$_3$ | 6-CH$_3$ | COCH$_3$ | CH$_3$ | H | 156–158 |
| 26 | CH$_3$ | CH$_3$ | 6-CH$_3$ | COC$_6$H$_5$ | CH$_3$ | H | 148–150 |
| 27 | CH$_3$ | CH$_3$ | 6-CH$_3$ | COCH$_3$ | C$_6$H$_5$ | H | 125–127 |
| 28 | CH$_3$ | CH$_3$ | 6-CH$_3$ | COCF$_3$ | CH$_3$ | H | 164–167 |
| 29 | CH$_3$ | CH$_3$ | 6-CH$_3$ | COCH$_3$ | CHCl$_2$ | H *) | 2.12(s, 6H), 3.60 (s, 2H), 6.83(s, 2H) |
| 30 | CH$_3$ | CH$_3$ | 6-CH$_3$ | COCHCl$_2$ | CH$_3$ | | 6.93(s, 2H), mixture |
| 31 | CH$_3$ | CH$_3$ | 6-CH$_3$ | H | C(CH$_3$)$_3$ | H | 261–263 |
| 32 | CH$_3$ | CH$_3$ | 6-CH$_3$ | CH$_3$ | CH$_3$ | H | 160–162 |
| 33 | CH$_3$ | CH$_3$ | 6-CH$_3$ | CH(CH$_3$)$_2$ | CH$_3$ | H | 135–137 |
| 34 | CH$_3$ | CH$_3$ | 6-CH$_3$ | H | CH$_3$ | H | 261–263 |
| 35 | CH$_3$ | CH$_3$ | 6-CH$_3$ | C$_2$H$_5$ | CH$_3$ | H | 1.11(t, J=3Hz, 3H) 2.44(q, J=3Hz, 2H) 6.95(s, 2H) |
| 36 | CH$_3$ | CH$_3$ | 6-CH$_3$ | C$_8$H$_{17}$ | CH$_3$ | H | 0.88(t, J=3, 2Hz, 3H) 1.21–1.62(m, 12H) 2.40(t, J=2, 4Hz, 2H) 6.80(s, 2H) |
| 37 | CH$_3$ | CH$_3$ | 6-CH$_3$ | C$_3$H$_7$ | C$_2$H$_5$ | H | 1.00(t, J=3, 7Hz, 3H) 1.13(t, J=3, 7Hz, 3H) 2.10(s, 6H), 2.29 (s, 3H |

TABLE 1-continued

Structure (I): phenyl ring with substituents Y, X, (Z)$_n$ attached to a pyranone ring system with OG, A, B substituents.

| Example No. | X | Y | (Z)$_n$ | A | B | G | M.p.(°C.) $^1$H NMR(CDCl$_3$) [ppm], δ: |
|---|---|---|---|---|---|---|---|
| 38 | CH$_3$ | CH$_3$ | 6-CH$_3$ | CH$_3$–CH–C$_2$H$_5$ | C$_2$H$_5$ *) | H | 0.80–1.05(m), 1.20–1.38(m), 1.98(s, 3H) (mixture) |
| 39 | CH$_3$ | CH$_3$ | 6-CH$_3$ | CH$_3$ | CH$_2$CHC$_2$H$_5$ \| CH$_3$ | H | |
| 40 | CH$_3$ | CH$_3$ | 6-CH$_3$ | CH(CH$_3$)$_2$ | CH$_2$CH(CH$_2$)$_3$ | H | 1.00(d, J=3Hz, 6H) 1.29(d, J=3Hz, 6H) 2.50(d, J=3Hz, 2H) 3.00(quintet, J=3Hz, 1H) |
| 41 | CH$_3$ | CH$_3$ | 6-CH$_3$ | H | CH$_2$OCOCH$_3$ | H | 185–186 |
| 42 | CH$_3$ | CH$_3$ | 6-CH$_3$ | 4-Cl—C$_6$H$_4$—S— | CH$_3$ | H | 2.10(s, 6H), 2.28(s, 3H) 2.56(s, 3H), 7.08 and 7.23(AB System, J=4, 5Hz, 4H) |
| 43 | CH$_3$ | CH$_3$ | 6-CH$_3$ | CH$_2$C$_6$H$_5$ | CH$_3$ | H | 2,07(s, 6H), 2.25 (s, 3H), 2.29(s, 3H) 3.80(s, 2H) |
| 44 | CH$_3$ | CH$_3$ | 6-CH$_3$ | C$_2$H$_5$ | CH$_3$ | H | 155–157 |
| 45 | CH$_3$ | CH$_3$ | 6-CH$_3$ | H | CH=CH—C$_6$H$_5$ | H | m.p. 122–124 |
| 46 | CH$_3$ | CH$_3$ | 6-CH$_3$ | H | C$_6$H$_5$ | H | 306–308 |
| 47 | CH$_3$ | CH$_3$ | 6-CH$_3$ | H | 2-Cl—C$_6$H$_4$ | H | 245–247 |
| 48 | CH$_3$ | CH$_3$ | 6-CH$_3$ | H | 2-CH$_3$-4-CH$_3$—C$_6$H$_3$ | H | 238–240 |
| 49 | CH$_3$ | CH$_3$ | 6-CH$_3$ | H | 3-CF$_3$—C$_6$H$_4$ | H | 258–260 |
| 50 | CH$_3$ | CH$_3$ | 6-CH$_3$ | H | 3-NO$_2$-4-CH$_3$—C$_6$H$_3$ | H | 228–230 |
| 51 | CH$_3$ | CH$_3$ | 6-CH$_3$ | H | 2-F—C$_6$H$_4$ | H | 246–248 |
| 52 | CH$_3$ | CH$_3$ | 6-CH$_3$ | H | 4-F—C$_6$H$_4$ | H | >300 |
| 53 | CH$_3$ | CH$_3$ | 6-CH$_3$ | H | 4-Cl—C$_6$H$_4$ | H | >300 |
| 54 | CH$_3$ | CH$_3$ | 6-CH$_3$ | H | 2-CH$_3$-4-CH$_3$-5-CH$_3$—C$_6$H$_2$ | H | 239–241 |
| 55 | CH$_3$ | CH$_3$ | 6-CH$_3$ | C$_2$H$_5$ | C$_6$H$_5$ | H | 193–195 |
| 56 | CH$_3$ | CH$_3$ | 6-CH$_3$ | H | 2-furyl | H | 254–255 |
| 57 | CH$_3$ | CH$_3$ | 6-CH$_3$ | H | 3-methyl-2,5-dimethylfuryl (H$_3$C–[furan]–CH$_3$ with CH$_3$ at 3-position) | H | 264–266 |
| 58 | CH$_3$ | CH$_3$ | 6-CH$_3$ | H | 2-thienyl (methyl-substituted) | H | 292–294 |
| 59 | CH$_3$ | CH$_3$ | 6-CH$_3$ | H | 3-methyl-2-thienyl | H | 321–324 |
| 60 | CH$_3$ | CH$_3$ | 6-CH$_3$ | H | 3,4-dichloro-5-methyl-2-thienyl | H | 299–301 |
| 61 | CH$_3$ | CH$_3$ | 6-CH$_3$ | H | 5-chloro-2-methyl-thienyl | H | 310–312 |
| 62 | CH$_3$ | CH$_3$ | 6-CH$_3$ | H | 2,5-dimethyl-3-methyl-thienyl | H | 246 |

TABLE 1-continued

| Example No. | X | Y | (Z)$_n$ | A | B | G | M.p.(°C.) $^1$H NMR(CDCl$_3$) [ppm], δ: |
|---|---|---|---|---|---|---|---|
| 63 | CH$_3$ | CH$_3$ | 6-CH$_3$ | H | 3-pyridyl | H | 266–268 |
| 64 | CH$_3$ | CH$_3$ | 6-CH$_3$ | H | 4-pyridyl | H | 268–270 |
| 65 | CH$_3$ | CH$_3$ | 6-CH$_3$ | H | 2,3,4,6-tetramethylpyridyl | H | 292–294 |
| 66 | CH$_3$ | CH$_3$ | 6-CH$_3$ | C$_6$H$_5$ | C$_2$H$_5$ | H | 1.24(t, J=3, 8Hz, 3H) 3.90(s, 2H), 6.78 (s, 2H), mixture |
| 67 | CH$_3$ | CH$_3$ | 6-CH$_3$ | CH$_3$ | CH$_2$C$_6$H$_5$ | * | |
| 68 | CH$_3$ | CH$_3$ | 6-CH$_3$ | —(CH$_2$)$_4$— | | H | 174–176 |
| 69 | CH$_3$ | CH$_3$ | 6-CH$_3$ | —(CH$_2$)$_3$— | | H | 241–243 |
| 70 | CH$_3$ | CH$_3$ | 6-CH$_3$ | —S—(CH$_2$)$_2$— | | H | 204–206 |
| 71 | CH$_3$ | CH$_3$ | 6-CH$_3$ | —CH$_2$O(CH$_2$)$_2$— | | H | 193–195 |
| 72 | CH$_3$ | CH$_3$ | 6-CH$_3$ | —CH$_2$S(CH$_2$)$_2$— | | H | 204–206 |
| 73 | CH$_3$ | CH$_3$ | 6-CH$_3$ | —CO$_2$—CH$_2$— | | H | 228–230 |
| 74 | CH$_3$ | CH$_3$ | 6-CH$_3$ | —CH(CH$_3$)—(CH$_2$)$_3$— | | H | 1.13(d, J=3Hz, 3H) 1.20(d, J=3Hz, 3H) 2.11(s, 6H), 2.13 (s, 6H); mixture |
| 75 | CH$_3$ | CH$_3$ | 6-CH$_3$ | —(CH$_2$)$_2$—CH(CH$_3$)—CH$_2$— | | H | |
| 76 | CH$_3$ | CH$_3$ | 6-CH$_3$ | —CH$_2$—CH(CH$_3$)—(CH$_2$)$_2$— | | H | 1.10(d, J=3, 7Hz, 3H) 2.10(s, 6H), 2.28 (s, 3H) |
| 77 | CH$_3$ | CH$_3$ | 6-CH$_3$ | —(CH$_2$)$_5$— | | H | 147–149 |
| 78 | CH$_3$ | CH$_3$ | 6-CH$_3$ | CO$_2$C$_2$H$_5$ | CH$_3$ | COC(CH$_3$)$_3$ | 124–127 |
| 79 | CH$_3$ | CH$_3$ | 6-CH$_3$ | CO$_2$C$_2$H$_5$ | CH$_3$ | COCH(CH$_3$)$_3$ | 118–120 |
| 80 | CH$_3$ | CH$_3$ | 6-CH$_3$ | CH$_3$ | CH$_3$ | COC(CH$_3$)$_3$ | 159–162 |
| 81 | CH$_3$ | CH$_3$ | 6-CH$_3$ | CH$_3$ | CH$_3$ | COCH$_3$ | 116–118 |
| 82 | CH$_3$ | CH$_3$ | 6-CH$_3$ | CH$_3$ | CH$_3$ | COCH(CH$_3$)$_2$ | 112–114 |
| 83 | CH$_3$ | CH$_3$ | 6-CH$_3$ | H | C(CH$_3$)$_3$ | COC(CH$_3$)$_3$ | 126–128 |
| 84 | CH$_3$ | CH$_3$ | 6-CH$_3$ | H | C(CH$_3$)$_3$ | COCH$_3$ | 1.83(s, 9H), 2.28 (s, 3H), 6.03(s, 1H), 6.85(s, 2H) |
| 85 | CH$_3$ | CH$_3$ | 6-CH$_3$ | H | C(CH$_3$)$_3$ | COCH(CH$_3$)$_2$ | 182–185 |
| 86 | CH$_3$ | CH$_3$ | 6-CH$_3$ | CH(CH$_3$)$_2$ | CH$_3$ | COCH$_3$ | 1.23(d, J=3, 2Hz, 6H), 1.78(s, 3H), 2.38 (s, 3H), 2.93(quintet, J=3, 2Hz, 1H) |
| 87 | CH$_3$ | CH$_3$ | 6-CH$_3$ | CO$_2$C$_2$H$_5$ | CH$_3$ | CO$_2$C$_2$H$_5$ | 96–99 |
| 88 | CH$_3$ | CH$_3$ | 6-CH$_3$ | CH$_3$ | CH$_3$ | CO$_2$C$_2$H$_5$ | 1.08(t, J=2, 8Hz, 2H), 1.95(s, 3H), 2.10 (s, 3H), 2.33(s, 3H) |
| 89 | CH$_3$ | CH$_3$ | 6-CH$_3$ | H | C(CH$_3$)$_2$CH$_2$F | H | 211–214 |
| 90 | CH$_3$ | CH$_3$ | 6-CH$_3$ | H | C(CH$_3$)$_2$CH$_2$OC$_2$H$_5$ | H | 167–168 |
| 91 | CH$_3$ | CH$_3$ | 6-CH$_3$ | H | C(CH$_3$)$_2$CH$_2$CN | H | 152–155 |
| 92 | CH$_3$ | CH$_3$ | 6-CH$_3$ | H | C(CH$_3$)$_2$CN | H | 243–246 |
| 93 | CH$_3$ | CH$_3$ | 6-CH$_3$ | H | C(CH$_3$)$_2$CHCl$_2$ | H | 187–190 |
| 94 | CH$_3$ | CH$_3$ | 6-CH$_3$ | H | C(CH$_3$)$_2$SC$_2$H$_5$ | H | 171–173 |
| 95 | CH$_3$ | CH$_3$ | 6-CH$_3$ | H | C(CH$_3$)$_2$(CH$_2$)$_2$CN | H | 234–236 |

TABLE 1-continued

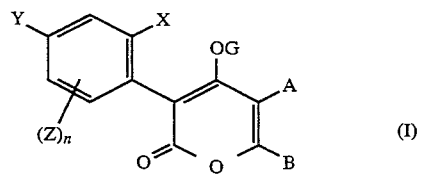

(I)

| Example No. | X | Y | (Z)$_n$ | A | B | G | M.p.(°C.) $^1$H NMR(CDCl$_3$) [ppm], δ: |
|---|---|---|---|---|---|---|---|
| 96 | CH$_3$ | CH$_3$ | 6-CH$_3$ | H | C(CH$_3$)2OCOCH$_3$ | H | 172–175 |
| 97 | CH$_3$ | CH$_3$ | 6-CH$_3$ | H | △ | H | 293–295 |
| 98 | CH$_3$ | CH$_3$ | 6-CH$_3$ | H | 3-CH$_3$O—C$_6$H$_4$ | H | 207–208 |
| 99 | CH$_3$ | CH$_3$ | 6-CH$_3$ | H | 4-CH$_3$O—C$_6$H$_4$ | H | 267 |
| 100 | CH$_3$ | CH$_3$ | 6-CH$_3$ | H | 2,4-Cl$_2$—C$_6$H$_3$ | H | 268–270 |
| 101 | CH$_3$ | CH$_3$ | 6-CH$_3$ | H | 2,4,5-Cl$_3$—C$_6$H$_2$ | H | 95–97 |
| 102 | CH$_3$ | CH$_3$ | 6-CH$_3$ | H | 2,3,4-Cl$_3$—C$_6$H$_2$ | H | 269–271 |
| 103 | CH$_3$ | CH$_3$ | 6-CH$_3$ | H | C$_6$F$_5$ | H | 241 |
| 104 | CH$_3$ | CH$_3$ | 6-CH$_3$ | H | 2,4-Cl$_2$—C$_6$H$_3$ | H | 234–237 |
| 105 | CH$_3$ | CH$_3$ | 6-CH$_3$ | H | 2,4-Br$_2$—C$_6$H$_3$ | H | 300 |
| 106 | CH$_3$ | CH$_3$ | 6-CH$_3$ | CH$_3$ | C$_6$H$_5$ | H | 183 |
| 107 | CH$_3$ | CH$_3$ | 6-CH$_3$ | CH(CH$_3$)$_2$ | C$_6$H$_5$ | H | 166–169 |
| 108 | CH$_3$ | CH$_3$ | 6-CH$_3$ | C$_3$H$_7$ | C$_6$H$_5$ | H | 183–185 |
| 109 | CH$_3$ | CH$_3$ | 6-CH$_3$ | CH$_3$ | 4-F—C$_6$H$_9$ | H | 242–244 |
| 110 | CH$_3$ | CH$_3$ | 6-CH$_3$ | CH$_3$ | 4-Cl—C$_6$H$_9$ | H | 207–208 |
| 111 | CH$_3$ | CH$_3$ | 6-CH$_3$ | CH$_3$ | 3,4-Cl$_2$—C$_6$H$_3$ | H | 230–233 |
| 112 | CH$_3$ | CH$_3$ | 6-CH$_3$ | H | 4-CF$_3$—C$_6$H$_4$ | H | 318–320 |
| 113 | CH$_3$ | CH$_3$ | 6-CH$_3$ | H | 4-CF$_3$O—C$_6$H$_4$ | H | 269–271 |
| 114 | CH$_3$ | CH$_3$ | 6-CH$_3$ | H | 4-Cl-2-F—C$_6$H$_9$ | H | 293–295 |
| 115 | CH$_3$ | CH$_3$ | 6-CH$_3$ | H | 2,6-F$_2$—C$_2$H$_3$ | H | 248–250 |
| 116 | CH$_3$ | CH$_3$ | 6-CH$_3$ | C$_6$H$_5$ | CH$_3$ | H | 97–100 |
| 117 | CH$_3$ | CH$_3$ | 6-CH$_3$ | C$_6$H$_5$ | CH(CH$_3$)$_2$ | H | 143–145 |
| 118 | CH$_3$ | CH$_3$ | 6-CH$_3$ | 2-Cl—C$_6$H$_4$ | C(CH$_3$)(CH$_2$F)$_2$ | H | 259–261 |
| 119 | CH$_3$ | CH$_3$ | 6-CH$_3$ | 2-F—C$_6$H$_9$ | C(CH$_3$)(CH$_2$F)$_2$ | H | 210 |
| 120 | CH$_3$ | CH$_3$ | 6-CH$_3$ | 2-Cl—C$_6$H$_9$ | 2-Cl—C$_6$H$_9$ | H | 140 |
| 121 | CH$_3$ | CH$_3$ | 6-CH$_3$ | 2,4-Cl$_2$—C$_5$H$_3$ | C(CH$_3$)$_3$ | H | 214 |
| 122 | CH$_3$ | CH$_3$ | 6-CH$_3$ | 2-Cl—C$_6$H$_9$ | C(CH$_3$)$_3$9 | H | 167–170 |
| 123 | CH$_3$ | CH$_3$ | 6-CH$_3$ | F | C$_6$H$_5$ | H | 272–273 |
| 124 | CH$_3$ | CH$_3$ | 6-CH$_3$ | Cl | △Cl | H | 100–103 |
| 125 | CH$_3$ | CH$_3$ | 6-CH$_3$ | Cl | C(CH$_3$)$_2$CH(CH$_3$)$_2$ | H | 214-127 |
| 126 | CH$_3$ | CH$_3$ | 6-CH$_3$ | F | C(CH$_3$)$_3$ | H | 192–194 |
| 127 | CH$_3$ | CH$_3$ | 6-CH$_3$ | Cl | C(CH$_3$)$_3$ | H | 197–200 |
| 128 | CH$_3$ | CH$_3$ | 6-CH$_3$ | H | 2-pyridyl | H | 298–300 |
| 129 | CH$_3$ | CH$_3$ | 6-CH$_3$ | CH$_3$ | 4-pyridyl | H | 317–319 |
| 130 | CH$_3$ | CH$_3$ | 6-CH$_3$ | —C(CH$_3$)$_2$OC(CH$_3$)$_2$— | | H | 197–198 |
| 131 | CH$_3$ | CH$_3$ | 6-CH$_3$ | —(CH$_2$)$_3$CH[C(CH$_3$)$_3$]— | | H | 172–175 |
| 132 | CH$_3$ | CH$_2$ | 6-CH$_3$ | —CH$_2$CH[C(CH$_3$)$_3$](CH$_2$)$_2$— | | H | 188–191 |
| 133 | CH$_3$ | CH$_3$ | 6-CH$_3$ | —(CH$_2$)$_2$CH(CF$_3$)CH$_2$— | | H | 96 |
| 134 | CH$_3$ | CH$_3$ | 6-CH$_3$ | —(CH$_2$)$_3$CH(OCH$_3$)— | | H | 66–69 |
| 135 | CH$_3$ | CH$_3$ | 6-CH$_3$ | —(CH$_2$)$_3$CHCl— | | H | 156–158 |
| 136 | CH$_3$ | CH$_3$ | 6-CH$_3$ | —CH$_2$CH(OCH$_3$)(CH$_2$)$_2$— | | H | 182 |
| 137 | CH$_3$ | H | H | CH$_3$ | CH$_3$ | H | 152–155 |
| 138 | CH$_3$ | CH$_3$ | H | CH$_3$ | CH$_3$ | H | 187–189 |
| 139 | Cl | Cl | H | CH$_3$ | CH$_3$ | H | 226–229 |
| 140 | Cl | H | 6-Cl | CH$_3$ | CH$_3$ | H | 262–264 |
| 141 | CH$_3$ | CH$_3$ | 6-CH$_3$ | (CH$_2$)$_3$ | | CO$_2$CH$_3$ | 136–138 |

TABLE 1-continued

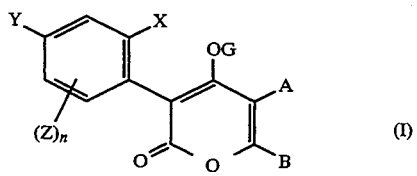

(I)

| Example No. | X | Y | (Z)$_n$ | A | B | G | M.p.(°C.) $^1$H NMR(CDCl$_3$) [ppm], δ: |
|---|---|---|---|---|---|---|---|
| 142 | CH$_3$ | CH$_3$ | 6-CH$_3$ | (CH$_2$)$_3$ | | COCH$_3$ | 138-139 |
| 143 | CH$_3$ | CH$_3$ | 6-CH$_3$ | (CH$_2$)$_3$ | | COCH(CH$_3$)$_2$ | 132-134 |
| 144 | CH$_3$ | CH$_3$ | 6-CH$_3$ | (CH$_2$)$_3$ | | COC(CH$_3$)$_3$ | 156-158 |
| 145 | CH$_3$ | CH$_3$ | 6-CH$_3$ | (CH$_2$)$_3$ | | CO$_2$C$_2$H$_5$ | 140-142 |
| 146 | CH$_3$ | CH$_3$ | 6-CH$_3$ | H | C$_6$H$_5$ | COCH$_3$ | 163-165 |
| 147 | CH$_3$ | CH$_3$ | 6-CH$_3$ | H | C$_6$H$_5$ | CO$_2$CH$_3$ | 146-149 |
| 148 | CH$_3$ | CH$_3$ | 6-CH$_3$ | H | C$_6$H$_5$ | CO(CH$_2$)$_2$Cl | 101-104 |
| 149 | CH$_3$ | CH$_3$ | 6-CH$_3$ | H | 4-Cl—C$_6$H$_4$ | CO(CH$_2$)Cl | 103-105 |
| 150 | CH$_3$ | CH$_3$ | 6-CH$_3$ | H | CH$_3$ | COCH$_3$ | 112-113 |
| 151 | CH$_3$ | CH$_3$ | 6-CH$_3$ | H | CH$_3$ | CO$_2$CH$_3$ | 134-136 |
| 152 | CH$_3$ | CH$_3$ | 6-CH$_3$ | H | CH$_3$ | CO(C(CH$_3$)$_3$ | 102-104 |

*)mixture

Preparation of the starting compounds of the formula (III)

EXAMPLE (III-1)

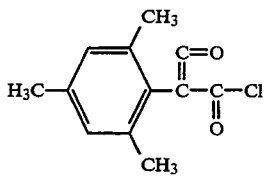

444.5 g (2 mol) of mesitylmalonic acid are suspended in 1000 ml of methylcyclohexane at 75°-80° C., and 714 g (6 mol) of thionyl chloride are added dropwise in the course of 3 hours. The mixture is subsequently heated slowly to a higher temperature, and stirring is continued for 8 hours at a bath temperature of 110°-120° C., using a reflux condenser.

Excess thionyl chloride is distilled off together with the solvent at 10 mbar at a bath temperature of up to 80° C., and when cold, the residue is diluted with 3 times the amount of petroleumether, filtered, concentrated and distilled.

373 g (84% of theory) of mesitylchlorocarbonylketene of boiling point 96°/0.45 mbar are obtained.

The remaining starting compounds of the formula (III) can be prepared analogously to Example (III-1) taking into consideration information in the description of the processes according to the invention.

EXAMPLE A

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with mustard beetle larvae (Phaedon cochleariae) while the leaves are still moist.

After the specified periods of time, the destruction in % is determined. 100% means that all the beetle larvae have been killed; 0% means that none of the beetle larvae have been killed.

In this test, a destruction of 100% was shown, after 7 days, for example, by the compounds of Preparation Examples 46, 47 and 65 at an exemplary active compound concentration of 0.1%.

EXAMPLE B

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the diamond-back moth (Plutella maculipennis) while the leaves are still moist.

After the specified periods of time, the destruction in % is determined. 100% means that all the caterpillars have been killed; 0% means that none of the caterpillars have been killed.

In this test, a destruction of 100% was shown, after 7 days, for example, by the compounds of Preparation Examples 38, 46, 52, 53, 61, 81 and 88 at an exemplary active compound concentration of 0.1%.

EXAMPLE C

Nephotettix test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza satira*) are treated by being dipped into the preparation of active compound of the desired concentration and are infested with larvae of the green rice cicada (*Nephotettix cincticeps*) while the seedlings are still moist.

After the specified period of time, the destruction in % is determined. 100% means that all the cicadas have been killed; 0% means that none of the cicadas have been killed.

In this test, a destruction of 100% was shown, after 6 days, for example, by the compounds of Preparation Examples 3, 31, 32, 34, 35, 37, 51, 52, 56, 58, 62, 65, 68, 69, 71, 74, 84 and 85 at an exemplary active compound concentration of 0.1%.

EXAMPLE D

Aphis test (systemic action)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Vicia faba*) which are heavily infested with the black bean aphid (*Aphis fabae*) are each watered with 20 ml of the preparation of the active compound of the desired concentration in such a way that the preparation of active compound penetrates the soil without wetting the shoot. The active compound is taken up by the roots and translocated to the shoot.

After the specified period of time, the destruction in % is determined. 100% means that all the aphids have been killed; 0% means that none of the aphids have been killed.

In this test, a destruction of 100% is shown, for example, by the compounds of Preparation Examples 32 and 38 at an exemplary active compound concentration of 0.1%.

EXAMPLE E

Tetranychus test (OP resistant)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the common spider mite or greenhouse red spider mite (*Tetranychus urticae*) are treated by being dipped into the preparation of active compound of the desired concentration.

After the specified period of time, the destruction in % is determined. 100% means that all the spider mites have been killed; 0% means that none of the spider mites have been killed.

In this test, a destruction of 100% was shown, after 7 days, for example, by the compounds of the Preparation Examples 3, 31, 84, 85 and 88 at an exemplary active compound concentration of 0.01%.

EXAMPLE F

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the following results were obtained at an exemplary application rate of 500 g/ha, the active compounds being tolerated well to very well by soya beans:

| Plant | % Activity | Compound of Preparation Example No. |
|---|---|---|
| Digitaria | 90–100 | 31, 32, 33, 34, 35, 38, 46, 52, 53, 60, 62, 63, 68, 69, 81, 84, 88 |
| Echinochloa | 70–100 | 31, 32, 33, 34, 34, 37, 46, 38, 52, 53, 56, 63, 68, 69, 81, 84 |
| Panicum | 95–100 | 31, 32, 33, 34, 35, 37, 38, 46, 52, 53, 56, 60, 62, 63 68, 69, 81, 84, 88 |
| Setaria | 70–100 | 31, 32, 33, 34, 35, 37, 38, 52, 53, 56, 60, 63, 68, 69, 81, 84, 88 |

EXAMPLE G

Test with Lucilia cuprina resistant larvae
Emulsifier: 35 parts by weight of ethylene glycol-monomethyl ether 35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 Lucilia cuprina res. larvae are introduced into a test tube which contains approx. 1 cm$^3$ of horse meat and 0.5 ml of the preparation of active compound. After 24 hours, the degree of destruction is determined.

In this test, a degree of destruction of 100% was shown, for example, by the compounds of Preparation Examples 32, 38 and 46 at an exemplary active compound concentration of 1000 ppm.

EXAMPLE H

Trichinella spiralis in vitro
Trichina larvae are isolated from the muscles of mice and washed with 0.9% NaCl supplemented with 20 µg/ml sisomycin and 2 µg/ml of clotrimazole. The actual incubation for approximately 20 trichinas per measurement was effected in 2 ml of a solution consisting of 10 g Bacto Casitone, 5 g of yeast (yeast extract), 2.5 g of glucose, 0.4 g of KH$_2$PO$_4$, 0.4 g of K$_2$HPO$_4$ per 500 ml, pH 7.2, containing 10 μg/ml of sisomycin and 1 mg/ml of clotrimazole. 10 mg of the substance to be tested are dissolved in 0.5 ml of DMSO, and such an amount is added to the incubation medium that the end concentrations are 100, 10 and 1 μg/ml. After incubation for 5 days at 19° C., the test is evaluated. The following key is used for the evaluation: 0=no action, the number of live larvae and worms is lower than in the case of the control; 2=good action, dead trichinas can be found; 3=very good action, all trichinas are dead.

In this test, a very good action (100% destruction) was shown, for example, by the compounds of Preparation Examples 13, 14, 15, 18, 26, 37 and 56 at an exemplary active compound concentration of 100 ppm.

EXAMPLE I

Nippostrongylus in vitro

Nippostrongylus are isolated from the small intestine of rats and washed with 0.9% of NaCl supplemented with 29 μg/ml sisomycin and 2 μg/ml of clotrimazole. The actual incubation of in each case 5 male and female Nippostrongylus is carried out in 1.0 ml of medium used for determining the activity of acetylcholine esterase. Enzyme determination is by the method of Rapson et al., 1987 (E. B. Rapson, D. C. Jenkins, A. S. Chilwan), Improved detection of anthelmintic activity in vitro screen utilizing adult *Nippostrongylus brasiliensis*. Parasitol. Res. 1987 73, 190 to 191.

The following key is used for the assessment: 3=full activity, 100% inhibition of the enzyme; 2=good activity, more than 75% inhibition; 1=poor activity, less than 50% inhibition.

In this test, a full activity (100% inhibition) was shown, for example, by the compound of Preparation Example 1 at an exemplary active compound concentration of 100 ppm.

We claim:

1. A 3-aryl-pyrone of the formula

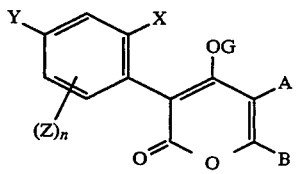

in which

A represents hydrogen; halogen; a radical selected from the group consisting of $C_1$-$C_{10}$-alkyl, $C_3$-$C_{10}$-alkenyl, $C_3$-$C_{10}$-alkinyl and $C_3$-$C_{10}$-cycloalkyl, each of which is optionally substituted by halogen; a radical selected from the group consisting of phenyl, naphthyl, hetaryl, phenyl-$C_1$-$C_6$-alkyl and hetaryl-$C_1$-$C_6$-alkyl, each of which is optionally substituted by at least one of halogen, nitro, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy and CN; or represents the group —$COR^1$, —$CO_2R^1$, —CN, —$CONR^1R^2$, —$SO_2R^1$ or —$P(O)(OR^1)(OR^2)$, in which $R^1$ and $R^2$ independently of one another represent hydrogen; a radical selected from the group consisting of $C_1$-$C_{10}$-alkyl and $C_3$-$C_{10}$-alkenyl, each of which is optionally substituted by halogen; or represent a radical selected from the group consisting of phenyl, naphthyl, hetaryl, phenyl-$C_1$-$C_6$-alkyl and hetaryl-$C_1$-$C_6$-alkyl, each of which is optionally substituted by at least one of halogen, nitro, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy and CN; or $R^1$ and $R^2$ together represent a $C_2$-$C_7$-alkylene group which is optionally interrupted by nitrogen, oxygen or sulphur;

B represents hydrogen; a radical selected from the group consisting of $C_1$-$C_{10}$-alkyl, $C_3$-$C_{10}$-alkenyl, $C_3$-$C_{10}$-alkinyl and $C_3$-$C_{10}$-cycloalkyl which are optionally substituted by halogen, CN, $C_1$-$C_6$-alkoxy, $C_1$-$C_6$-alkylthio, $C_1$-$C_6$-alkylcarbonyloxy or phenyl; or represents a radical selected from the group consisting of phenyl, naphthyl, hetaryl, phenyl-$C_1$-$C_6$-alkyl and hetaryl-$C_1$-$C_6$-alkyl which are optionally substituted by at least one of halogen, CN, nitro, $C_1$-$C_8$-alkyl, $C_1$-$C_8$-alkoxy, $C_1$-$C_8$-alkylthio, $C_1$-$C_8$-halogenoalkyl and $C_1$-$C_8$-halogenoalkoxy, or A and B together represent a straight chain or branched $C_2$-$C_7$-alkylene group which is optionally substituted by at least one of $C_1$-$C_8$-alkyl, $C_1$-$C_6$-halogenoalkyl, $C_1$-$C_6$-halogenoalkyl, $C_1$-$C_6$-alkoxy, $C_1$-$C_6$-alkylthio and halogen and which is optionally interrupted by nitrogen, sulphur, oxygen or —O—CO—;

X represents halogen, $C_1$-$C_6$-alkyl or $C_1$-$C_6$-alkoxy;

Y represents hydrogen, halogen, $C_1$-$C_6$-alkyl, $C_1$-$C_6$-alkoxy or $C_1$-$C_6$-halogenoalkyl;

Z represents hydrogen, halogen, $C_1$-$C_6$-alkyl or $C_1$-$C_6$-alkoxy;

n represents 1 or 2;

G represents hydrogen, —$COR^3$,

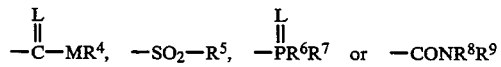

$R^3$ represents a radical selected from the group consisting of $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, $C_1$-$C_8$-polyalkoxy-$C_1$-$C_8$-alkyl and $C_3$-$C_8$-cycloalkyl which is optionally interrupted by at least one of oxygen and sulphur, each of these radicals optionally being substituted by halogen; phenyl which is optionally substituted by at least one of halogen, nitro, $C_1$-$C_6$-alkyl, $C_1$-$C_6$-alkoxy, $C_1$-$C_6$-halogenoalkyl and $C_1$-$C_6$-halogenoalkoxy; phenyl-$C_1$-$C_6$-alkyl which is optionally substituted by at least one of halogen, $C_1$-$C_6$-alkyl, $C_1$-$C_6$-alkoxy, $C_1$-$C_6$-halogenoalkyl and $C_1$-$C_6$-halogenoalkoxy; hetaryl which is optionally substituted by at least one of halogen and $C_1$-$C_6$-alkyl; phenoxy-$C_1$-$C_6$-alkyl which is optionally substituted by at least one of halogen and $C_1$-$C_6$-alkyl; or hetaryloxy-$C_1$-$C_6$-alkyl which is optionally substituted by at least one of halogen, amino and $C_1$-$C_6$-alkyl;

$R^4$ represents a radical selected from the group consisting of $C_1$-$C_{20}$-alkyl, $C_2$-$C_{20}$-alkenyl, $C_1$-$C_8$-alkoxy-$C_1$-$C_8$-alkyl and $C_1$-$C_8$-polyalkoxy-$C_1$-$C_8$-alkyl each of which is optionally substituted by halogen; or a radical selected from the group consisting of phenyl and benzyl each of which is optionally substituted by at least one of halogen, nitro, $C_1$-$C_6$-alkyl, $C_1$-$C_6$-alkoxy and $C_1$-$C_6$-halogenoalkyl;

$R^5$, $R^6$ and $R^7$ independently of one another represent a radical selected from the group consisting of $C_1$-$C_8$-alkyl, $C_1$-$C_8$-alkoxy, $C_1$-$C_8$-alkylthio, $C_1$-$C_8$-alkylamino, di-($C_1$-$C_8$)-alkylamino, $C_2$-$C_5$-alkenylthio, $C_2$-$C_5$-alkinylthio and $C_3$-$C_7$-cycloalkylthio each of which is optionally substituted by halogen; or represent a radical selected from the group consisting of phenyl, phenyloxy and phenylthio, each of which is optionally substituted by at least one of halogen, nitro, cyano, $C_1$-$C_4$-alkoxy, $C_1$-$C_4$-alkylthio, $C_1$-$C_1$-halogenoalkoxy, $C_1$-$C_4$-halogenoalkoxy, $C_1$-$C_4$-halogenoalkylthio, $C_1$-$C_4$-alkyl and $C_1$-$C_4$-halogenoalkyl;

$R^8$ and $R^9$ independently of one another represent hydrogen; a radical selected from the group consisting of $C_1$-$C_{20}$-alkyl, $C_1$-$C_{20}$-alkoxy, $C_3$-$C_{10}$-cycloalkyl, $C_2$-$C_8$-alkenyl and $C_1$-$C_8$-alkoxy-$C_1$-$C_8$-alkyl each of which is optionally substituted by halogen; or represent a radical selected from the group consisting of phenyl and benzyl each of which is optionally substituted by at least one of halogen, $C_1$-$C_{20}$-alkyl, $C_1$-$C_{20}$-halogenoalkyl and $C_1$-$C_{20}$-alkoxy; or $R^8$ and $R^9$ together form a $C_2$-$C_6$-alkylene group which is optionally interrupted by at least one of oxygen and sulphur;

L represents oxygen or sulphur and

M represents oxygen or sulphur, with the exception of the compound 2,4-pentadienoic acid, 3,5-dihydroxy-2-(o-methoxyphenyl)-5-phenyl-δ-lactone.

2. An aryl-pyrone according to claim 1, in which

A represents hydrogen; halogen; a radical selected from the group consisting of $C_1$-$C_8$-alkyl, $C_3$-$C_8$-alkenyl, $C_3$-$C_8$-alkinyl and $C_3$-$C_8$-cycloalkyl, each of which is optionally substituted by halogen; or represents a radical selected from the group consisting of phenyl, naphthyl, hetaryl, phenyl-$C_1$-$C_4$-alkyl and hetaryl-$C_1$-$C_4$-alkyl, each of which is optionally substituted by at least one of halogen, nitro, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkoxy and CN, or represents the group —COR$^1$, —CO$_2$R$^1$, —CN, —CONR$^1$R$^2$, —SO$_2$R$^1$ or —P(O)(OR$^1$)(OR$^2$), in which $R^1$ and $R^2$ independently of one another represent hydrogen; a radical selected from the group consisting of $C_1$-$C_8$-alkyl and $C_3$-$C_8$-alkenyl, which are optionally substituted by halogen; a radical selected from the group consisting of phenyl, hetaryl, phenyl-$C_1$-$C_4$-alkyl and hetaryl-$C_1$-$C_4$-alkyl, which is optionally substituted by at least one of halogen, nitro, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkoxy and CN; or $R^1$ and $R^2$ together represent a $C_2$-$C_6$-alkylene group which is optionally interrupted by nitrogen, oxygen or sulphur;

B represents hydrogen; a radical selected from the group consisting of $C_1$-$C_8$-alkyl, $C_3$-$C_8$-alkenyl, $C_3$-$C_8$-alkinyl and $C_3$-$C_8$-cycloalkyl which are optionally substituted by halogen, $C_{1-4}$-alkoxy, $C_{1-4}$-alkylthio, $C_1$-$C_4$-alkylcarbonyloxy or phenyl; or represents a radical selected from the group consisting of phenyl, naphthyl, hetaryl, phenyl-$C_1$-$C_4$-alkyl and hetaryl-$C_1$-$C_4$-alkyl which are optionally substituted by at least one of halogen, CN, nitro, $C_1$-$C_6$-alkyl, $C_1$-$C_6$-alkoxy, $C_1$-$C_6$-alkylthio, $C_1$-$C_6$-halogenoalkyl and $C_1$-$C_6$-halogenoalkoxy; or A and B together represent a $C_2$-$C_6$-alkylene group which is optionally substituted by at least one of 1-5-halogen-$C_1$-$C_4$-alkyl, $C_1$-$C_4$-alkoxy, $C_1$-$C_4$-alkyl and halogen and which is optionally interrupted by nitrogen, sulphur, oxygen or —O—CO—, X represents halogen, $C_1$-$C_4$-alkyl or $C_1$-$C_4$-alkoxy;

Y represents hydrogen, halogen, $C_1$-$C_4$-alkyl, $C_1$-$C_4$-alkoxy or $C_1$-$C_4$-halogenoalkyl;

Z represents hydrogen, halogen, $C_1$-$C_4$-alkyl or $C_1$-$C_4$-alkoxy;

n represents 1 or 2;

G represents hydrogen, —COR$^3$,

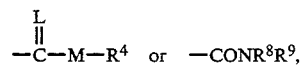

in which $R^3$ represents a radical selected from the group consisting of $C_1$-$C_{16}$-alkyl, $C_2$-$C_{16}$-alkenyl, $C_1$-$C_6$-alkoxy-$C_1$-$C_6$-alkyl, $C_1$-$C_6$-alkylthio-$C_1$-$C_6$-alkyl, $C_1$-$C_6$-polyalkoxy-$C_1$-$C_6$-alkyl and $C_3$-$C_7$-cycloalkyl which is optionally interrupted by at least one of oxygen and sulphur, each of these radicals optionally being substituted by halogen; phenyl which is optionally substituted by at least one of halogen, nitro, $C_1$-$C_4$-alkyl, $C_1$-$C_4$-alkoxy, $C_1$-$C_3$-halogenoalkyl and $C_1$-$C_3$-halogenoalkoxy; phenyl-$C_1$-$C_4$-alkyl which is optionally substituted by at least one of halogen, $C_1$-$C_4$-alkyl, $C_1$-$C_4$-alkoxy, $C_1$-$C_3$-halogenoalkyl and $C_1$-$C_3$-halogenoalkoxy; hetaryl which is optionally substituted by at least one of halogen and $C_1$-$C_6$-alkyl; phenoxy-$C_1$-$C_5$-alkyl which is optionally substituted by at least one of halogen and $C_1$-$C_4$-alkyl; or hetaryloxy-$C_1$-$C_5$-alkyl which is optionally substituted by at least one of halogen, amino and $C_1$-$C_4$-alkyl;

$R^4$ represents a radical selected from the group consisting of $C_1$-$C_{16}$-alkyl, $C_2$-$C_{16}$-alkenyl, $C_1$-$C_{16}$-alkoxy-$C_1$-$C_6$-alkyl and $C_1$-$C_6$-polyalkoxy-$C_1$-$C_6$-alkyl which are optionally substituted by halogen, or represents a radical selected from the group consisting of phenyl and benzyl which are optionally substituted by at least one of halogen, nitro, $C_1$-$C_4$-alkyl, $C_1$-$C_3$-alkoxy and $C_1$-$C_3$-halogenoalkyl;

$R^8$ and $R^9$ independently of one another represent hydrogen, a radical selected from the group consisting of $C_1$-$C_{16}$-alkyl, $C_1$-$C_{16}$-alkoxy, $C_3$-$C_{16}$-cycloalkyl, $C_2$-$C_6$-alkenyl and $C_1$-$C_6$-alkoxy-$C_1$-$C_6$-alkyl which are optionally substituted by halogen, or represent a radical selected from the group consisting of phenyl and benzyl which are optionally substituted by at least one of halogen, $C_1$-$C_6$-alkyl, $C_1$-$C_6$-halogenoalkyl and $C_1$-$C_6$-alkoxy; or $R^8$ and $R^9$ together form a $C_2$-$C_6$-alkylene group which is optionally interrupted by at least one of oxygen and sulphur;

L represents oxygen or sulphur; and

M represents oxygen or sulphur.

3. A 3-aryl-pyrone according to claim 1, in which

A represents hydrogen; halogen; or a radical selected from the group consisting of $C_1$-$C_4$-alkyl, phenyl and benzyl which are optionally substituted by halogen;

B represents hydrogen, $C_1$-$C_4$-alkyl which is optionally substituted by halogen, CN, methoxy or methylthio, or represents a radical selected from the group consisting of phenyl, furyl, thiazolyl and pyridyl which are optionally substituted by at least one of halogen, nitro, $C_1$-$C_4$-alkyl and $C_1$-$C_4$-alkoxy;

A and B together form the group —$(CH_2)_3$—, —$(CH_2)_4$—, —$(CH_2)_5$—, —$CH_2$—$CH(CH_3)(CH_2)_2$—, —$CH_2O$—$(CH_2)_2$ or —$CH_2S(CH_2)_2$, each of which is optionally substituted by $CF_3$, Cl or methoxy;

X represents methyl;
Y represents methyl;
Z represents methyl; and
G represents hydrogen or $COR^3$ in which
$R^3$ represents $C_1$-$C_6$-alkyl or $C_1$-$C_6$-alkoxy.

4. A compound according to claim 1 of the formula

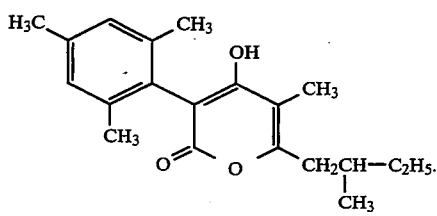

5. A compound according to claim 1 of the formula

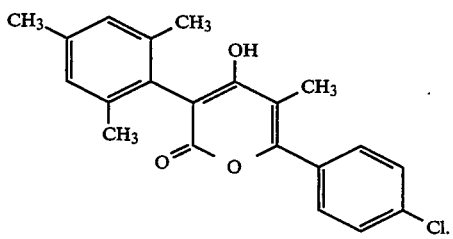

6. A compound according to claim 1 of the formula

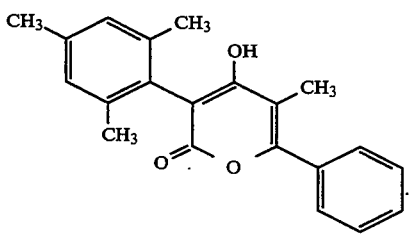

7. A compound according to claim 1 of the formula

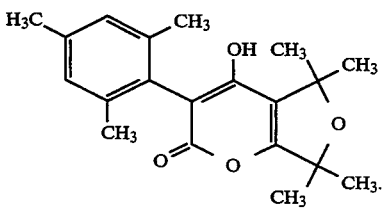

8. An arthropodicidal, nematicidal, parasiticidal, or herbicidal composition comprising an amount effective therefor of a compound according to claim 1 and a diluent.

9. A method of combating anthropods, nematodes, parasites or undesired vegetation which comprises applying thereto or to a locus from which it is desired they be excluded an amount effective therefor of a 3-arylpyrone of the formula

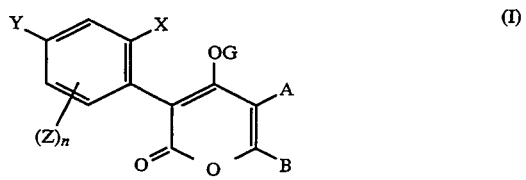

in which

A represents hydrogen; halogen; a radical selected from the group consisting of $C_1$-$C_{10}$-alkyl, $C_3$-$C_{10}$-alkenyl, $C_3$-$C_{10}$-alkinyl and $C_3$-$C_{10}$-cycloalkyl, each of which is optionally substituted by halogen; a radical selected from the group consisting of phenyl, naphthyl, hetaryl, phenyl-$C_1$-$C_6$-alkyl and hetaryl-$C_1$-$C_6$-alkyl, each of which is optionally substituted by at least one of halogen, nitro, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy and CN; or represents the group —$COR^1$, —$CO_2R^1$, —CN, —$CONR^1R^2$, —$SO_2R^1$ or —$P(O)(OR^1)(OR^2)$, in which $R^1$ and $R^2$ independently of one another represent hydrogen; a radical selected from the group consisting of $C_1$-$C_{10}$-alkyl and $C_3$-$C_{10}$-alkenyl, each of which is optionally substituted by halogen; or represent a radical selected from the group consisting of phenyl, naphthyl, hetaryl, phenyl-$C_1$-$C_6$-alkyl and hetaryl-$C_1$-$C_6$-alkyl, each of which is optionally substituted by at least one of halogen, nitro, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy and CN; or $R^1$ and $R^2$ together represent a $C_2$-$C_7$-alkylene group which is optionally interrupted by nitrogen, oxygen or sulphur;

B represents hydrogen; a radical selected from the group consisting of $C_1$-$C_{10}$-alkyl, $C_3$-$C_{10}$-alkenyl, $C_3$-$C_{10}$-alkinyl and $C_3$-$C_{10}$-cycloalkyl which are optionally substituted by halogen, CN, $C_1$-$C_6$-alkoxy, $C_1$-$C_6$-alkylthio, $C_1$-$C_6$-alkylcarbonyloxy or phenyl; or represents a radical selected from the group consisting of phenyl, naphthyl, hetaryl, phenyl-$C_1$-$C_6$-alkyl and hetaryl-$C_1$-$C_6$-alkyl which are optionally substituted by at least one of halogen, CN, nitro, $C_1$-$C_8$-alkyl, $C_1$-$C_8$-alkoxy, $C_1$-$C_8$-alkylthio, $C_1$-$C_8$-halogenoalkyl and $C_1$-$C_8$-halogenoalkoxy, or A and B together represent a straight chain or branched $C_2$-$C_7$-alkylene group which is optionally substituted by at least one of $C_1$-$C_8$-alkyl, $C_1$-$C_6$-halogenoalkyl, $C_1$-$C_6$-halogenoalkyl, $C_1$-$C_6$-alkoxy, $C_1$-$C_6$-alkylthio and halogen and which is optionally interrupted by nitrogen, sulphur, oxygen or —O—CO—;

X represents halogen, $C_1$-$C_6$-alkyl or $C_1$-$C_6$-alkoxy;
Y represents hydrogen, halogen, $C_1$-$C_6$-alkyl, $C_1$-$C_6$-alkoxy or $C_1$-$C_6$-halogenoalkyl;
Z represents hydrogen, halogen, $C_1$-$C_6$-alkyl or $C_1$-$C_6$-alkoxy;
n represents 1 or 2;
G represents hydrogen, —$COR^3$,

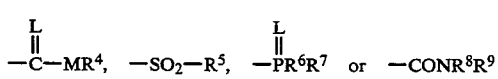

$R^3$ represents a radical selected from the group consisting of $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_1$–$C_8$-alkyl and $C_3$–$C_8$-cycloalkyl which is optionally interrupted by at least one of oxygen and sulphur, each of these radicals optionally being substituted by halogen; phenyl which is optionally substituted by at least one of halogen, nitro, $C_1$–$C_6$-alkyl, $C_1$–$C_6$-alkoxy, $C_1$–$C_6$-halogenoalkyl and $C_1$–$C_6$-halogenoalkoxy; phenyl-$C_1$–$C_6$-alkyl which is optionally substituted by at least one of halogen, $C_1$–$C_6$-alkyl, $C_1$–$C_6$-alkoxy, $C_1$–$C_6$-halogenoalkyl and $C_1$–$C_6$-halogenoalkoxy; hetaryl which is optionally substituted by at least one of halogen and $C_1$–$C_6$-alkyl; phenoxy-$C_1$–$C_6$-alkyl which is optionally substituted by at least one of halogen and $C_1$–$C_6$-alkyl; or hetaryloxy-$C_1$–$C_6$-alkyl which is optionally substituted by at least one of halogen, amino and $C_1$–$C_6$-alkyl;

$R^4$ represents a radical selected from the group consisting of $C_1$–$C_{20}$-alkyl, $C_2$–$C_{20}$-alkenyl, $C_1$–$C_8$-alkoxy-$C_1$–$C_8$-alkyl and $C_1$–$C_8$-polyalkoxy-$C_1$–$C_8$-alkyl each of which is optionally substituted by halogen; or a radical selected from the group consisting of phenyl and benzyl each of which is optionally substituted by at least one of halogen, nitro, $C_1$–$C_6$-alkyl, $C_1$–$C_6$-alkoxy and $C_1$–$C_6$-halogenoalkyl;

$R^5$, $R^6$ and $R^7$ independently of one another represent a radical selected from the group consisting of $C_1$–$C_8$-alkyl, $C_1$–$C_8$-alkoxy, $C_1$–$C_8$-alkylthio, $C_1$–$C_8$-alkylamino, di-($C_1$–$C_8$)-alkylamino, $C_2$–$C_5$-alkenylthio, $C_2$–$C_5$-alkinylthio and $C_3$–$C_7$-cycloalkylthio each of which is optionally substituted by halogen; or represent a radical selected from the group consisting of phenyl, phenyloxy and phenylthio, each of which is optionally substituted by at least one of halogen, nitro, cyano, $C_1$–$C_4$-alkoxy, $C_1$–$C_4$-alkylthio, $C_1$–$C_4$-halogenoalkoxy, $C_1$–$C_4$-halogenoalkoxy, $C_1$–$C_4$-halogenoalkylthio, $C_1$–$C_4$-alkyl and $C_1$–$C_4$-halogenoalkyl;

$R^8$ and $R^9$ independently of one another represent hydrogen; a radical selected from the group consisting of $C_1$–$C_{20}$-alkyl, $C_1$–$C_{20}$-alkoxy, $C_3$–$C_{10}$-cycloalkyl, $C_2$–$C_8$-alkenyl and $C_1$–$C_8$-alkoxy-$C_1$–$C_8$-alkyl each of which is optionally substituted by halogen; or represent a radical selected from the group consisting of phenyl and benzyl each of which is optionally substituted by at least one of halogen, $C_1$–$C_{20}$-alkyl, $C_1$–$C_{20}$-halogenoalkyl and $C_1$–$C_{20}$-alkoxy; or $R^8$ and $R^9$ together form a $C_2$–$C_6$-alkylene group which is optionally interrupted by at least one of oxygen and sulphur;

L represents oxygen or sulphur and

M represents oxygen or sulphur.

10. The method according to claim 9, wherein such compound is

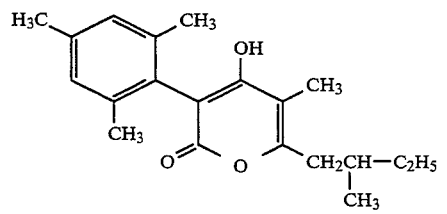

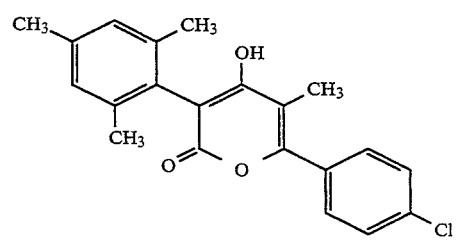

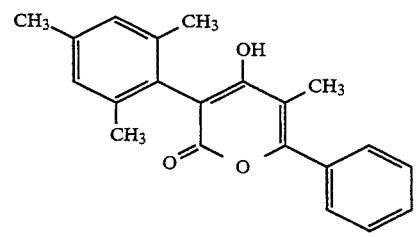

or

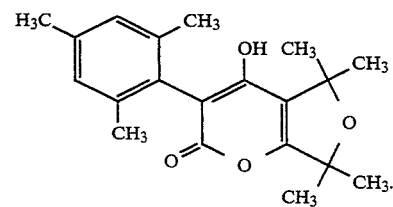

* * * * *